United States Patent [19]
Howland et al.

[11] Patent Number: 5,928,232
[45] Date of Patent: *Jul. 27, 1999

[54] SPINAL FIXATION SYSTEM

[75] Inventors: Robert S. Howland, Seal Beach; James A. Rinner, Fountain Valley; Shawn R. Tebbe, Fullerton, all of Calif.

[73] Assignee: Advanced Spine Fixation Systems, Incorporated, Irvine, Calif.

[*] Notice: This patent issued on a continued prosecution application filed under 37 CFR 1.53(d), and is subject to the twenty year patent term provisions of 35 U.S.C. 154(a)(2).

[21] Appl. No.: 08/628,143

[22] Filed: Apr. 4, 1996

Related U.S. Application Data

[63] Continuation-in-part of application No. 08/340,640, Nov. 16, 1994, abandoned.

[51] Int. Cl.⁶ .................................................. A61B 17/70
[52] U.S. Cl. ................................................ 606/61; 606/72
[58] Field of Search ................................ 606/61, 60, 72, 606/73, 53; 623/17

[56] References Cited

U.S. PATENT DOCUMENTS

| | | | |
|---|---|---|---|
| 4,085,744 | 4/1978 | Lewis et al. | 606/61 |
| 4,269,178 | 5/1981 | Keene | 606/61 |
| 4,361,141 | 11/1982 | Tanner | 606/61 |

(List continued on next page.)

FOREIGN PATENT DOCUMENTS

| | | |
|---|---|---|
| 537598 | 4/1993 | European Pat. Off. . |
| 3032237 | 3/1982 | Germany . |
| 1424825 | 9/1988 | Russian Federation . |
| 1465041 | 3/1989 | Russian Federation . |
| 1516104 | 10/1989 | Russian Federation . |
| 1517955 | 10/1989 | Russian Federation . |
| 1614805 | 12/1990 | Russian Federation . |
| 2131300 | 6/1984 | United Kingdom . |

OTHER PUBLICATIONS

"Biomechanical Studies," ISOLA Spinal Implant System, Jan. 1991, pp. IV–1 to IV–14, author unknown.
"Biomechanics of the Spine: Clinical and Surgical Perspective," pp. 269–285. Author and Date unknown.
"Cotrel–Dubousset Instrumentation." SOFAMOR, Rang du Fliers, France, date and author unknown.

(List continued on next page.)

*Primary Examiner*—Guy V. Tucker
*Attorney, Agent, or Firm*—Christie, Parker, & Hale, LLP

[57] ABSTRACT

A spinal fixation system utilizing grapple hooks comprising a lower hook attached to the lamina on the caudal-side of a vertebra and an upper hook attached to the lamina on the cranial-side of a vertebra. The hooks clamp the vertebra lamina in the center. Thus, the hooks clamp the lamina at the spinous process which is the strongest part of the lamina. Bolts are provided for attaching the lower hook to the upper hook to thereby attach the lower and upper hooks to the vertebra and clamps for attaching the lower and upper hooks to spine rods. A spinal fixation kit is provided with a plurality of uniquely configured fixation systems to assure satisfactory fit to any vertebra of any patient, and specially designed tools are preferably provided to aide in a method of implanting the systems thereby reducing the time required for implantation.

36 Claims, 18 Drawing Sheets

U.S. PATENT DOCUMENTS

| | | | |
|---|---|---|---|
| 4,382,438 | 5/1983 | Jacobs | 606/61 |
| 4,409,968 | 10/1983 | Drummond | 606/61 |
| 4,411,259 | 10/1983 | Drummond | 606/61 |
| 4,422,451 | 12/1983 | Kalamchi | 606/61 |
| 4,433,676 | 2/1984 | Bobechko | 606/61 |
| 4,573,454 | 3/1986 | Hoffman | 606/61 |
| 4,653,481 | 3/1987 | Howland et al. | 606/61 |
| 4,686,970 | 8/1987 | Dove et al. | 606/61 |
| 4,697,582 | 10/1987 | William | 606/61 |
| 4,738,251 | 4/1988 | Plaza | 606/61 |
| 4,790,303 | 12/1988 | Steffee | 606/61 |
| 4,815,453 | 3/1989 | Cotrel | 606/61 |
| 4,854,304 | 8/1989 | Zielke | 606/61 |
| 4,998,936 | 3/1991 | Mehdian | 606/61 |
| 5,005,562 | 4/1991 | Cotrel | 606/61 |
| 5,010,879 | 4/1991 | Moriya et al. | 606/61 |
| 5,024,213 | 6/1991 | Asher et al. | 606/61 |
| 5,030,220 | 7/1991 | Howland | 606/61 |
| 5,074,864 | 12/1991 | Cozad et al. | 606/61 |
| 5,102,412 | 4/1992 | Rogonzinski | 606/61 |
| 5,116,334 | 5/1992 | Cozad et al. | 606/61 |
| 5,181,917 | 1/1993 | Rogozinski | 606/61 |
| 5,242,446 | 9/1993 | Steffee et al. | 606/61 |
| 5,246,442 | 9/1993 | Ashman et al. | 606/61 |
| 5,257,993 | 11/1993 | Ashler et al. | 606/61 |
| 5,261,913 | 11/1993 | Marnay | 606/61 |
| 5,334,203 | 8/1994 | Wagner | 606/61 |
| 5,360,429 | 11/1994 | Jeanson et al. | 606/61 |
| 5,380,326 | 1/1995 | Lin | 606/61 |
| 5,395,370 | 3/1995 | Miller et al. | 606/61 |
| 5,415,659 | 5/1995 | Lee et al. | 606/61 |
| 5,439,463 | 8/1995 | Lin | 606/61 |
| 5,542,946 | 8/1996 | Logroscino et al. | 606/61 |

OTHER PUBLICATIONS

Dubousset, "Cotrel–Dubousset Instrumentation for Paralytic Neuromuscular Spinal Deformities with Emphasis on Pelvic Obliquity," pp. 347–364, date unknown.

"Edwards Modular Spinal System," Scientific Spinal, LTd., Baltimore, Maryland (containing except from An & Cotler (eds), Spinal Instrumentation, Williams and Wilkens, Dec. 1992, pp. 303–324):

Gurr et al., "cotrel–Dubousset Instrumentation in Adults, A Preliminary Report," Spine, vol. 13, No. 5 (Dec. 1988) pp. 510–520.

Rogozinski et al., "Rogozinski Spinal Rod System," Smith & Nephew Richards, Inc, Memphis, Tennessee, pp. 1–19, date unknown.

Shufflebarger, "Sacral Instrumentation– Cotrel–Dubousset," Groupe International CD, GICD, (May 14, 1986) pp. 1–8.

"Surgical Management of Thoracic and Lumbar Burst Fractures," Spinal Surgery, vol. 2, p. 945, Author and date unknown.

Wisnewski et al., "Biomechanical Analysis, Rogozinski Spinal Rod System," Smith & Nephew Richards, Inc., Memphis, Tennessee. date unknown.

"Z Product Encyclopedia," Zimmer– USA, Inc., (1978), p. B203. Author unknown.

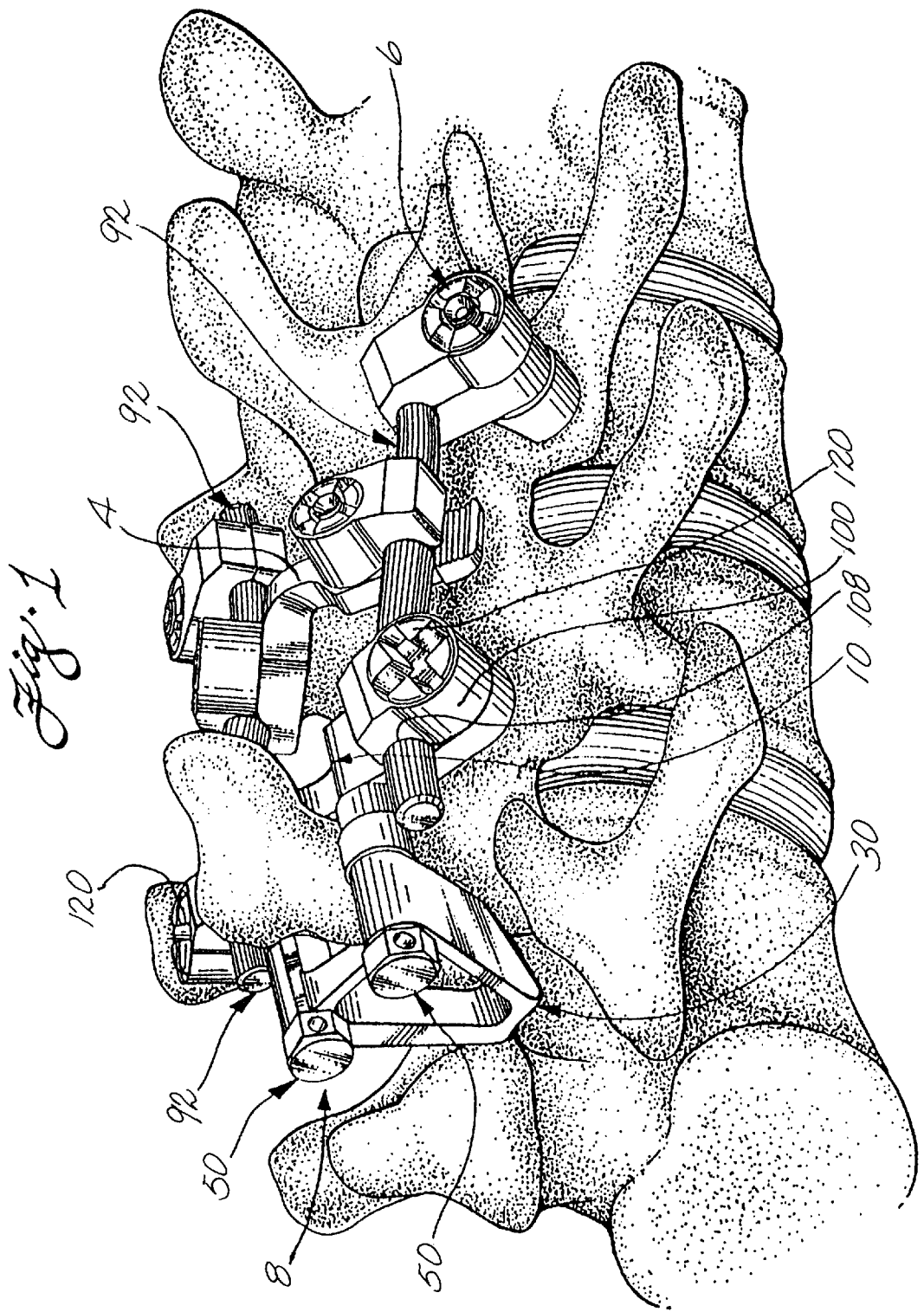

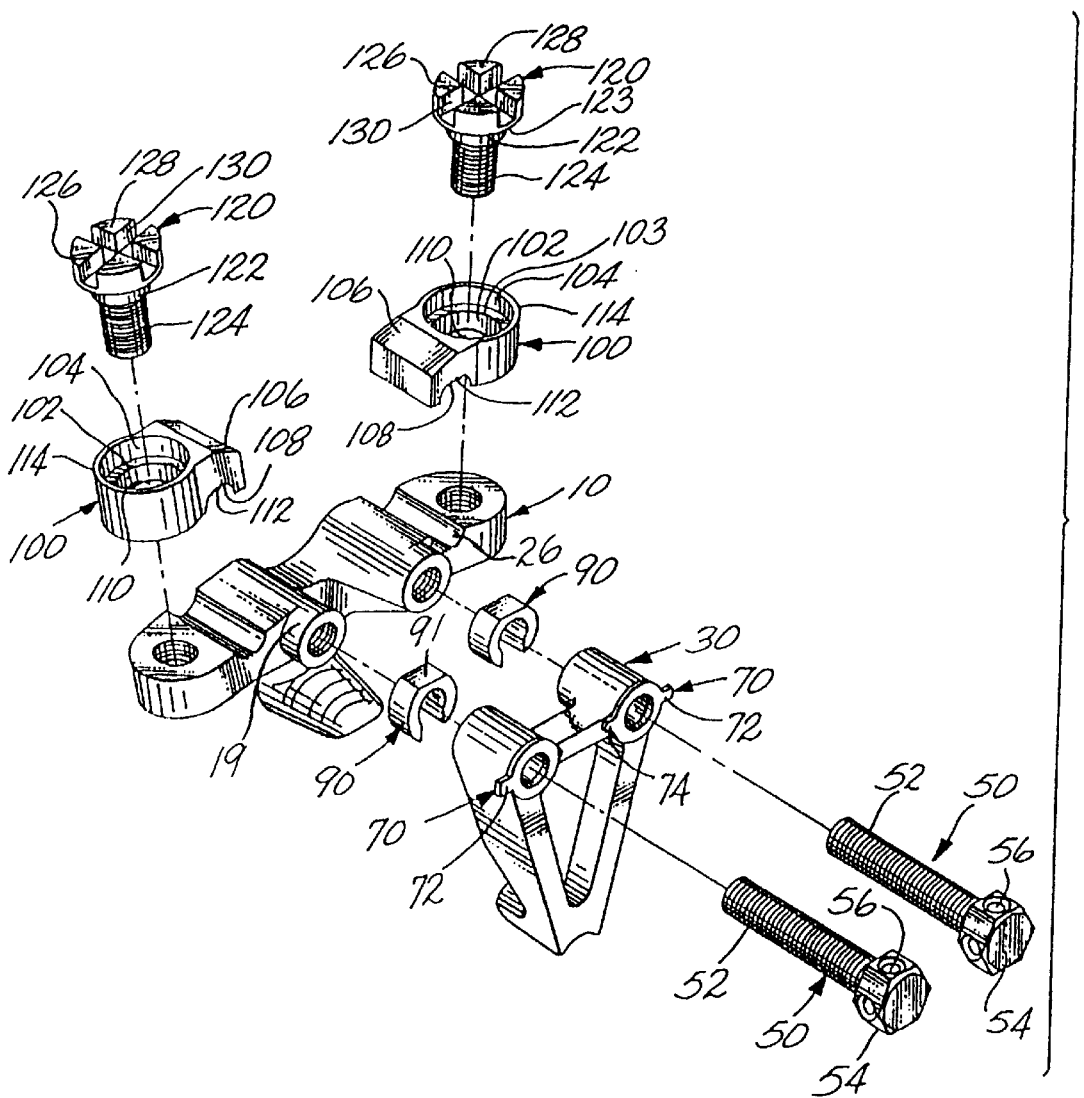

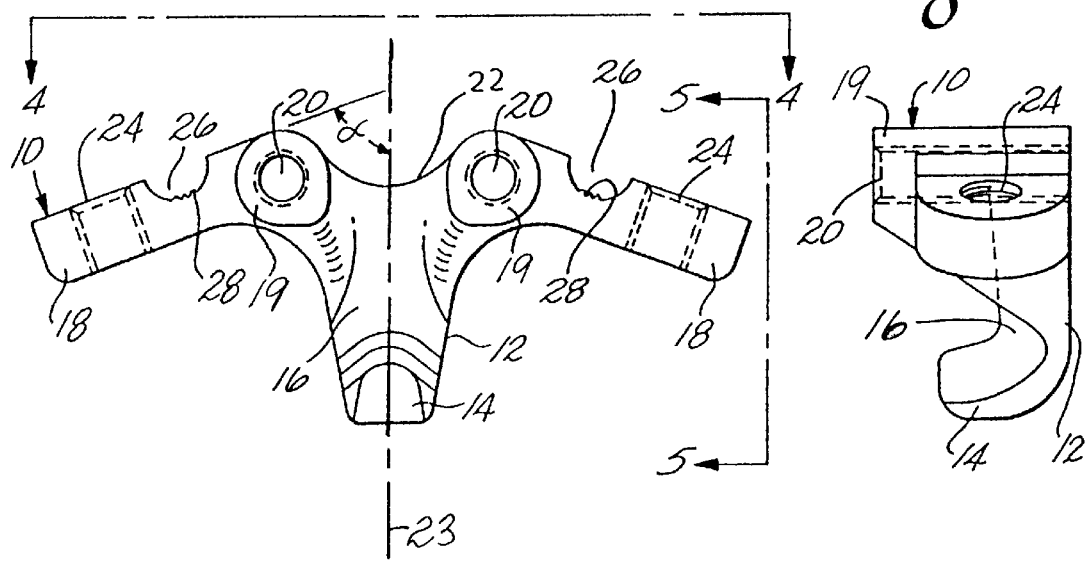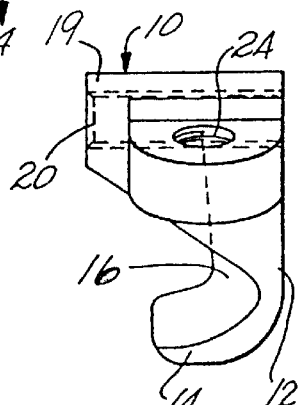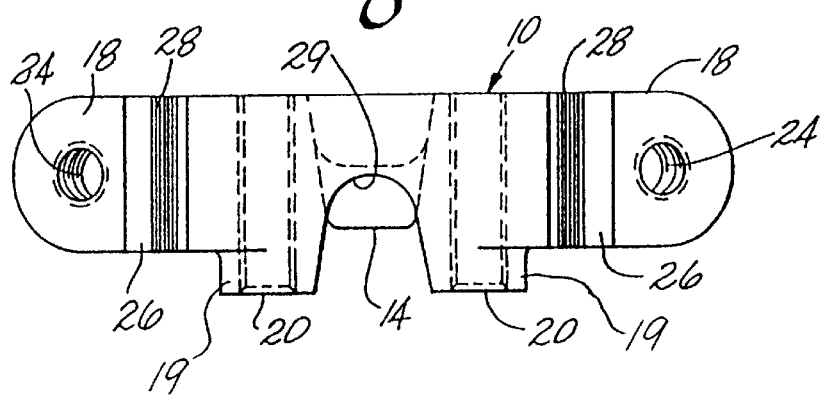

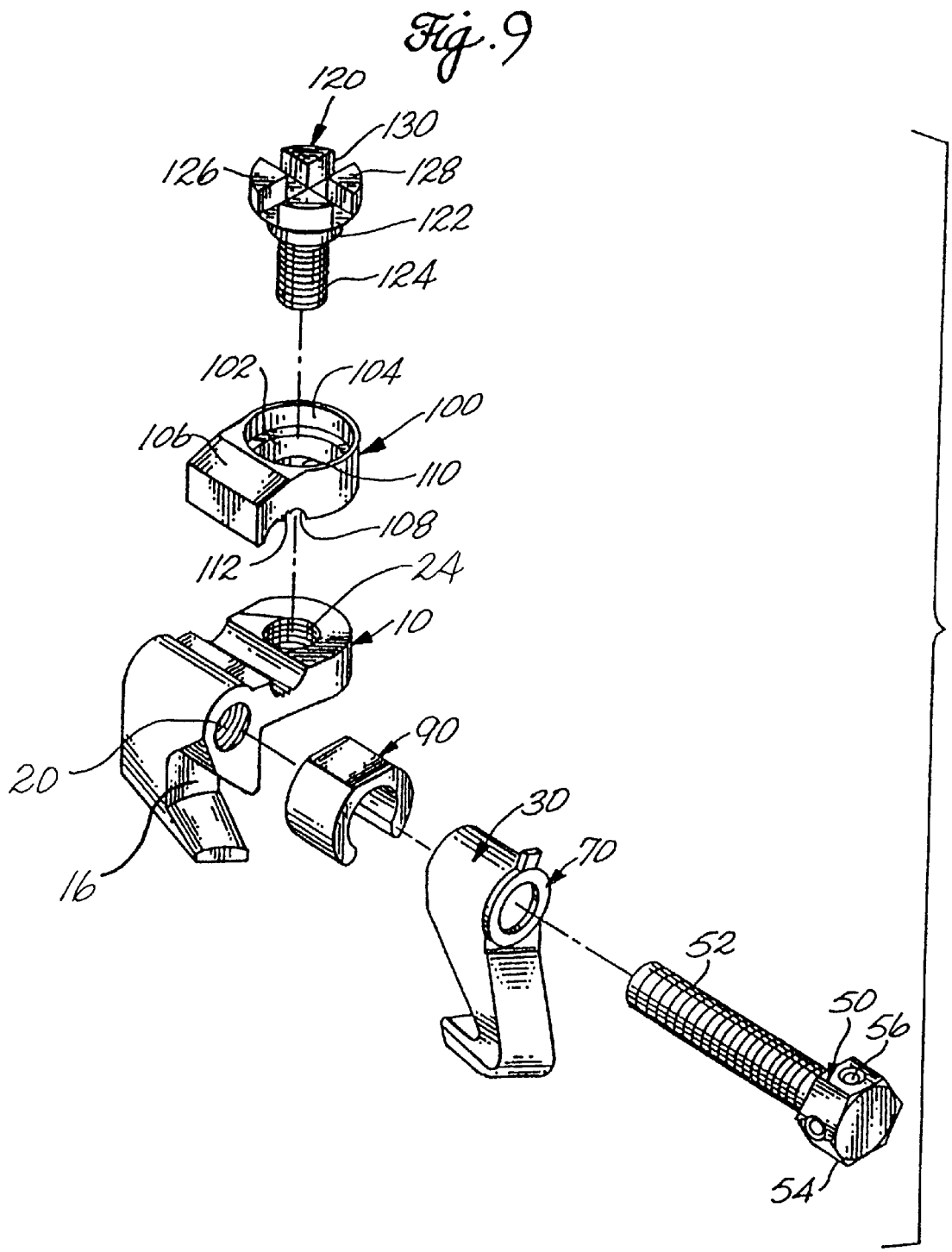

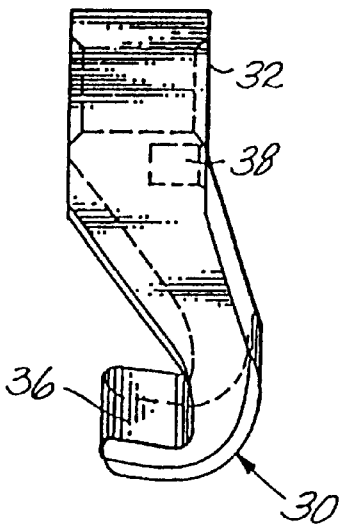
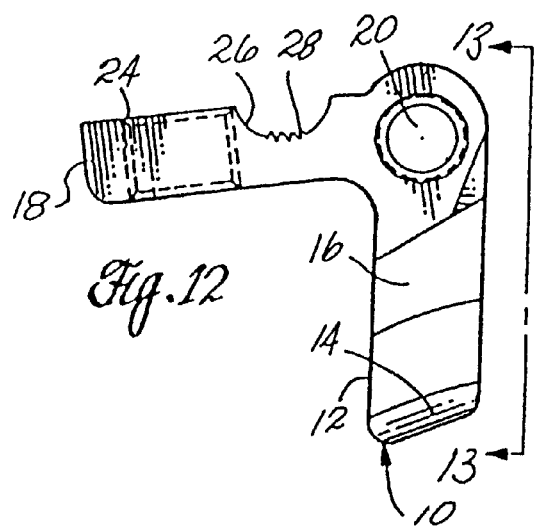
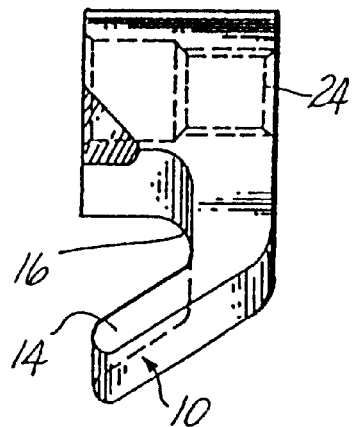
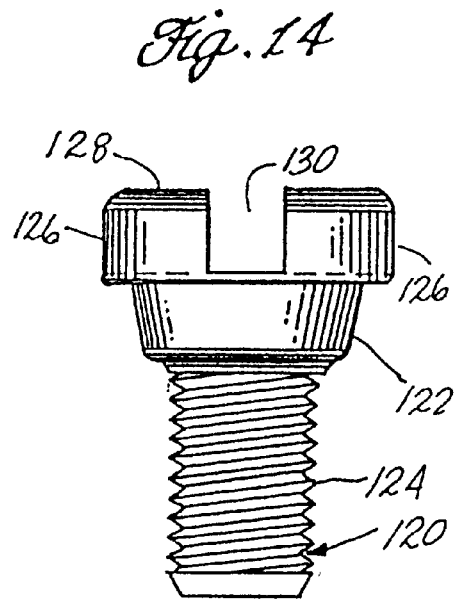

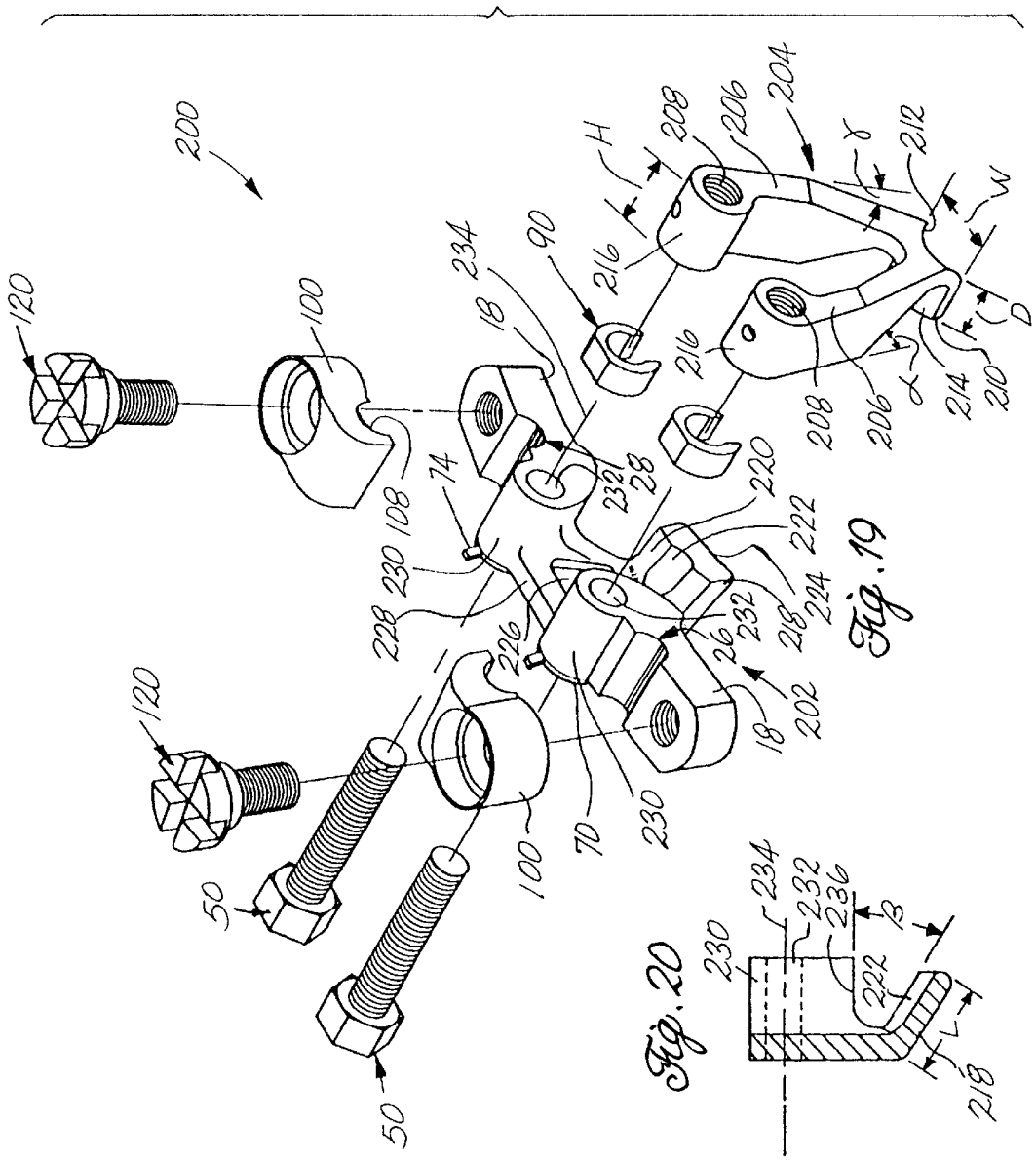

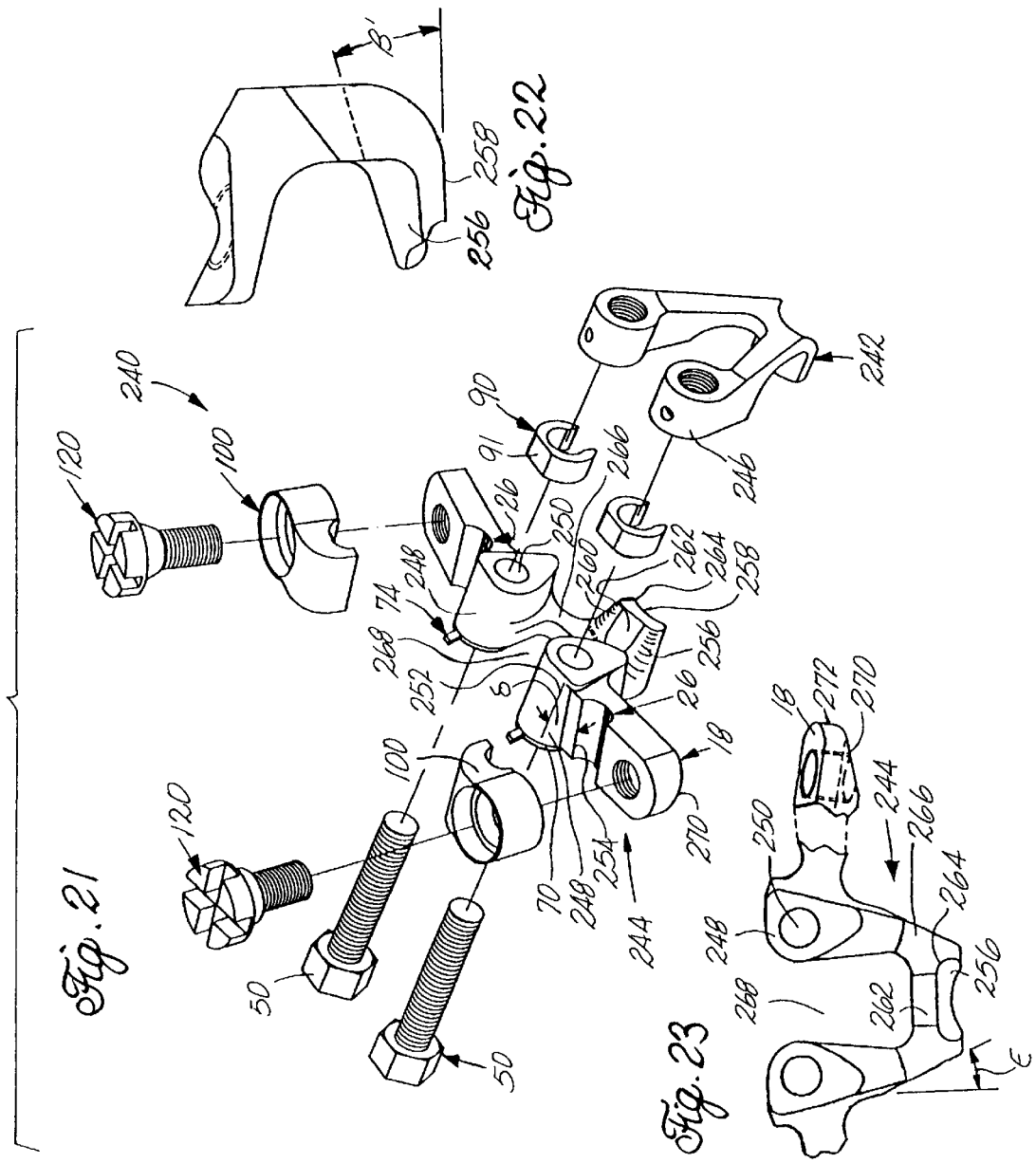

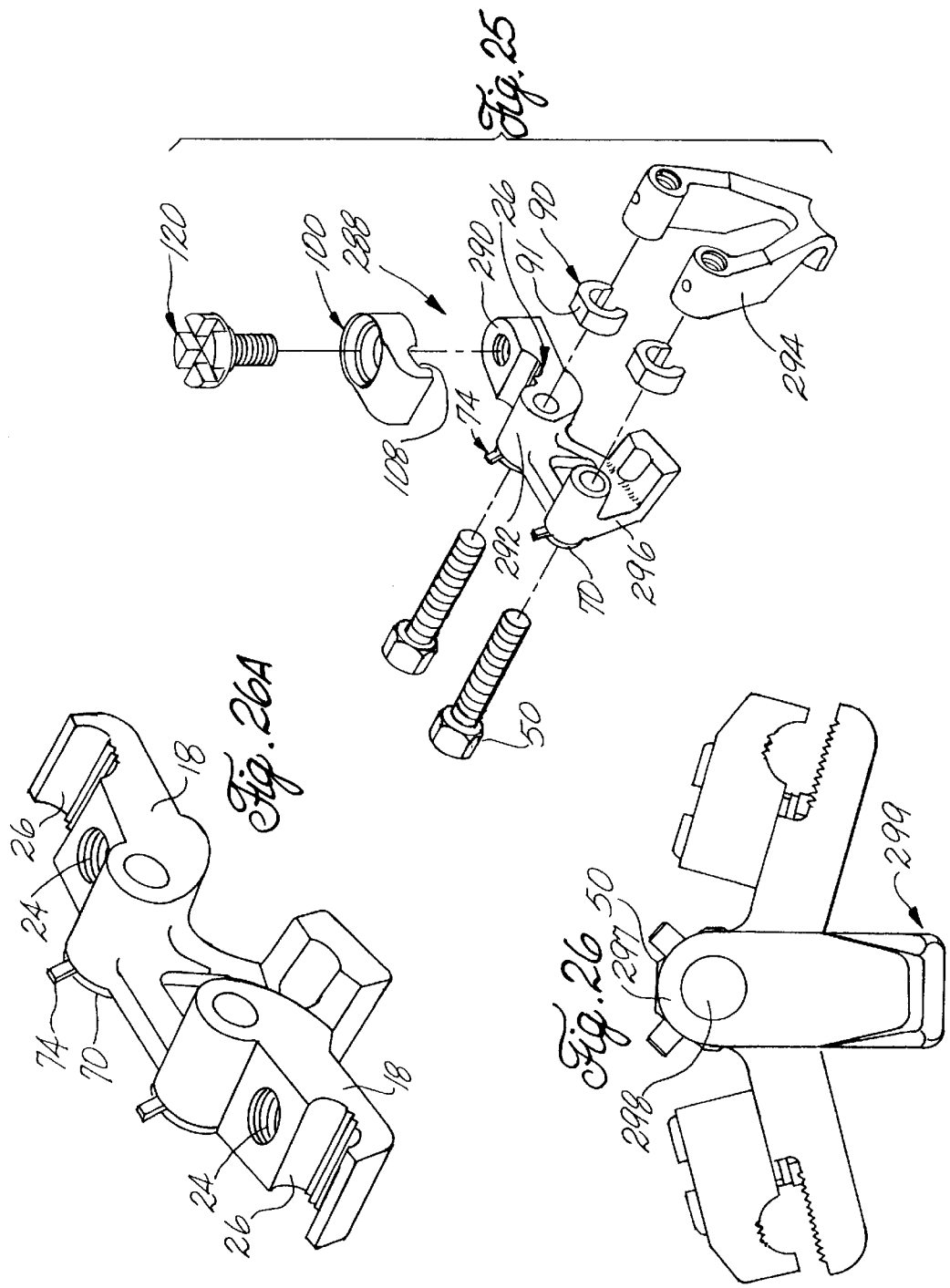

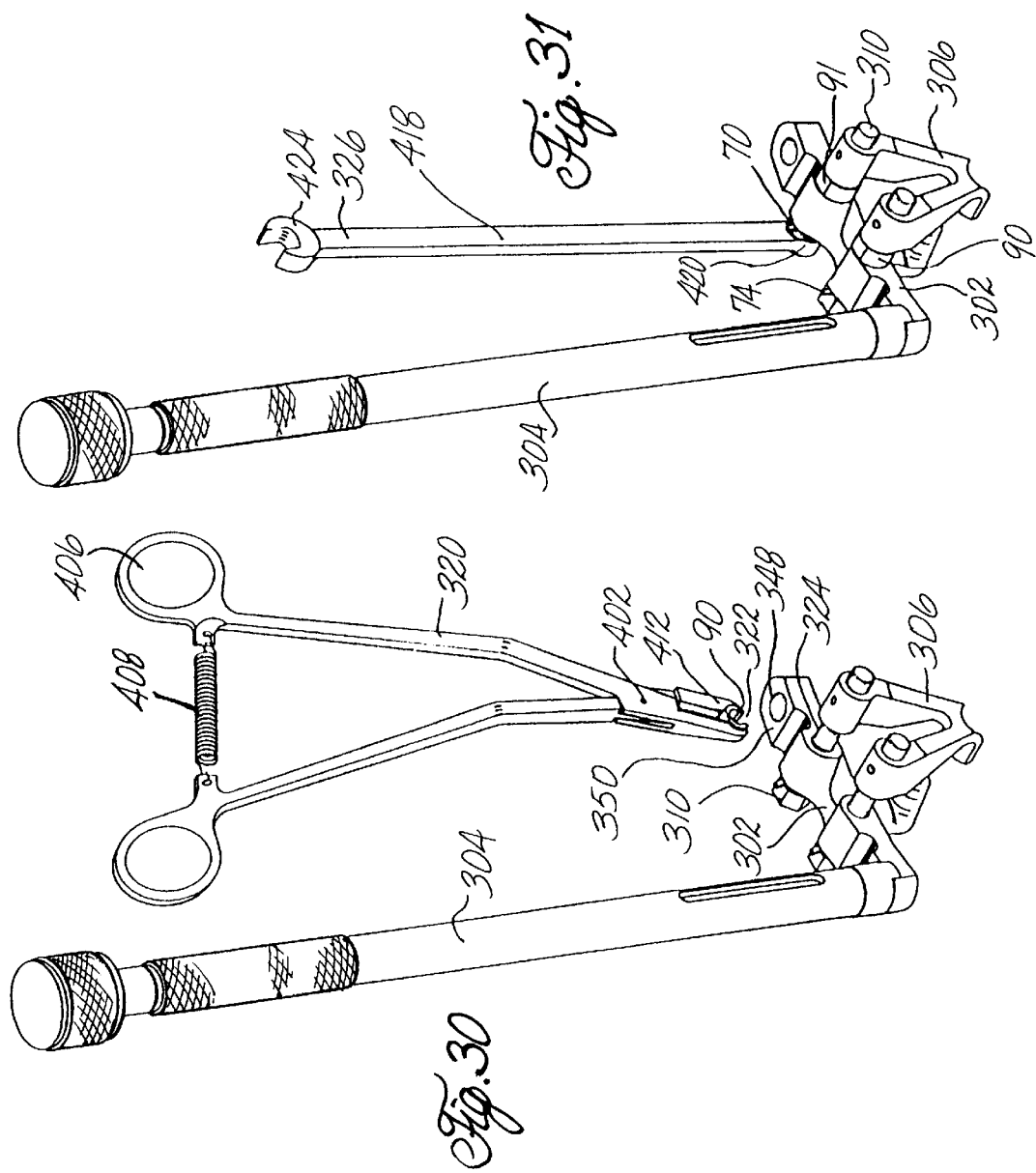

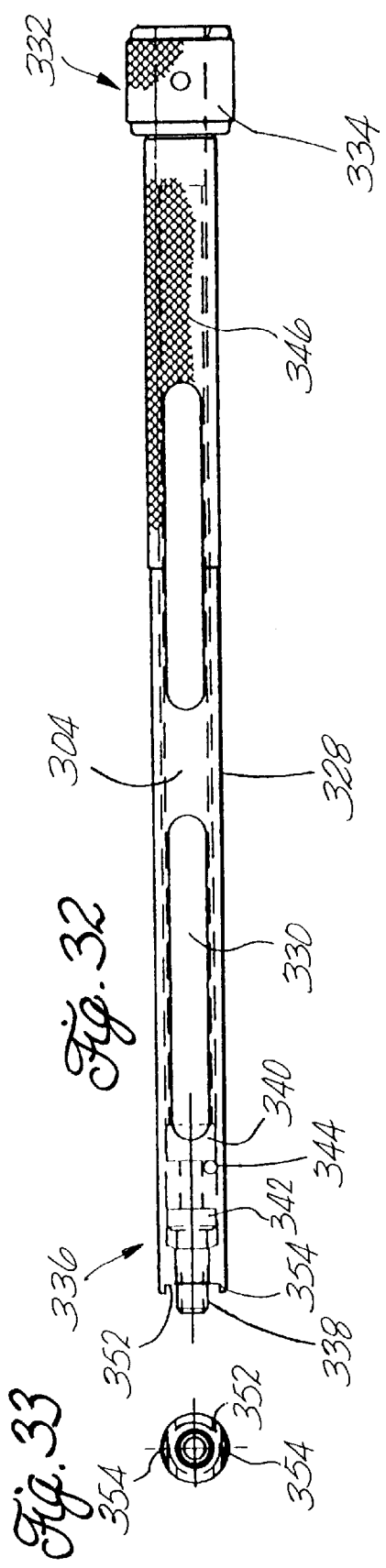

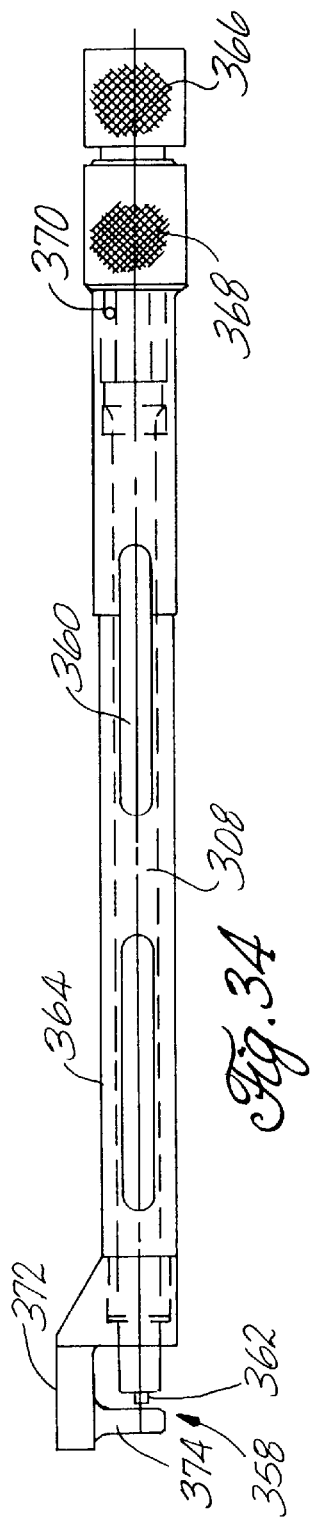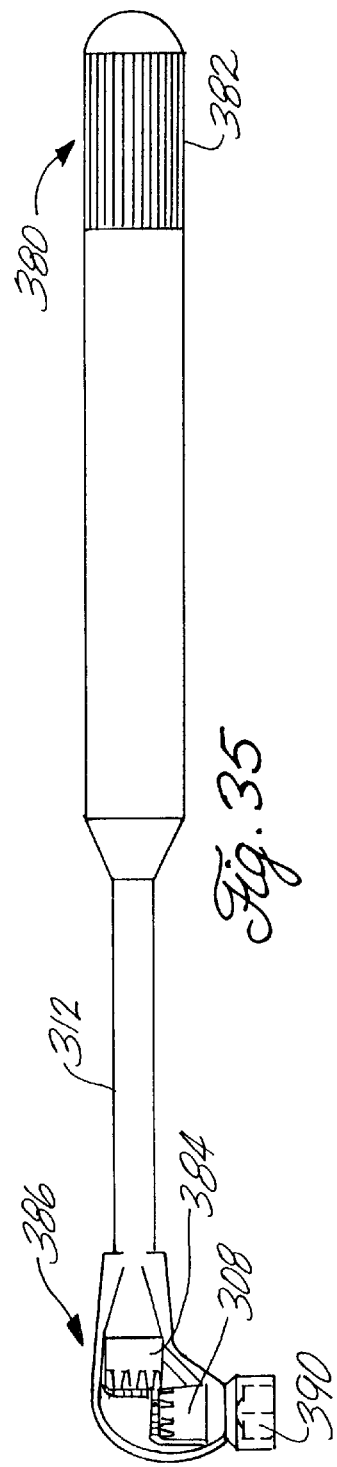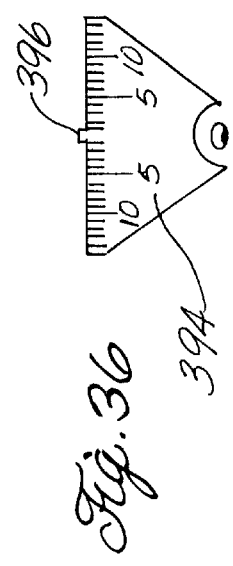

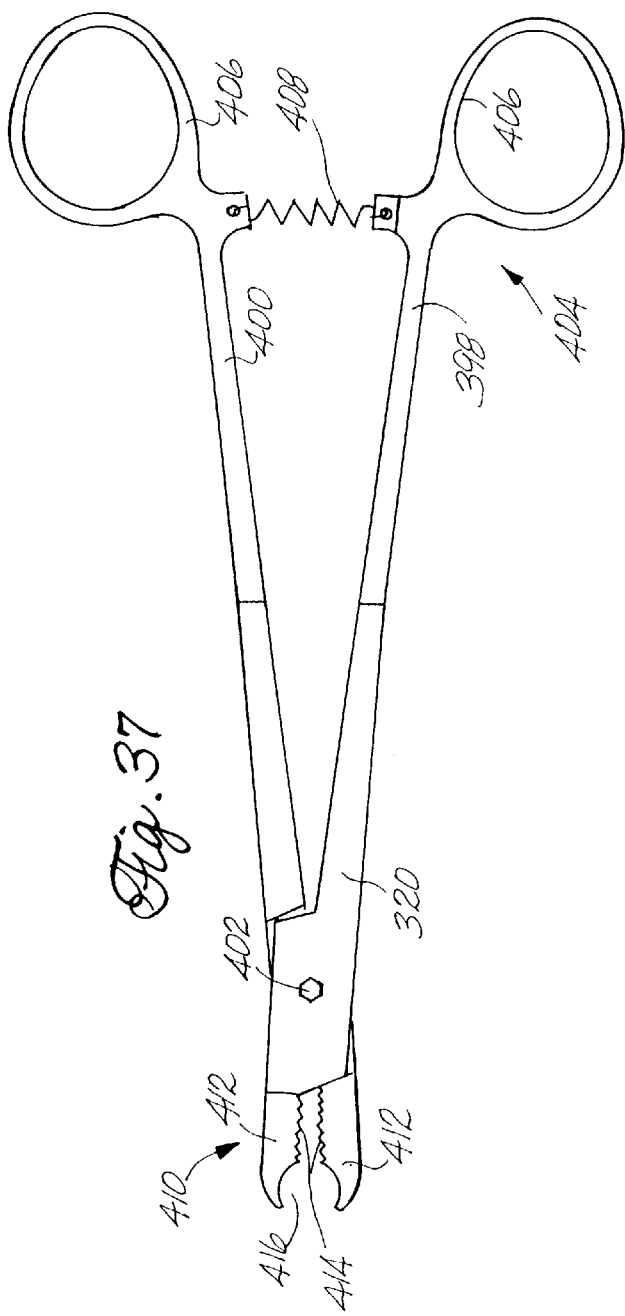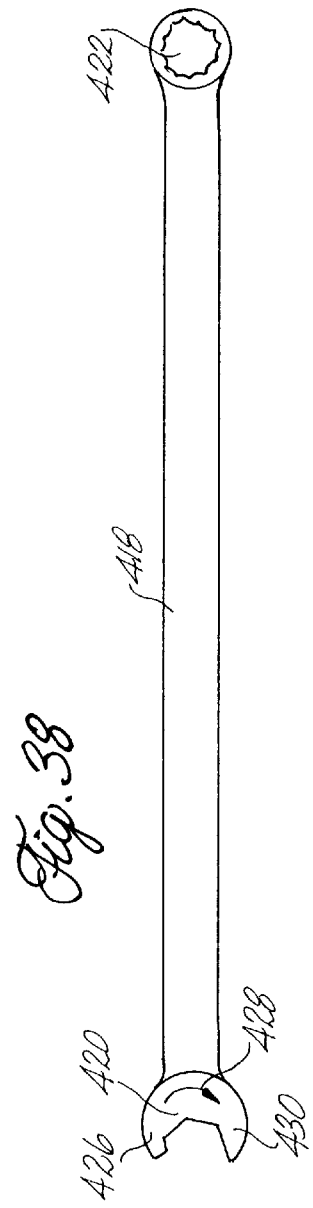

SPINAL FIXATION SYSTEM

RELATED APPLICATION

This application is a continuation-in-part of U.S. application Ser. No. 08/340,640, filed Nov. 16, 1994, now abandoned, which is fully incorporated herein by reference.

FIELD OF THE INVENTION

This invention relates to an implantable spinal fixation system for the surgical treatment of spinal disorders. More specifically, it relates to a clamping system which reduces damage to the vertebra of the spine and increases stability when installed.

BACKGROUND OF THE INVENTION

Various types of spinal column disorders are known and include scoliosis (abnormal lateral curvature of the spine), kyphosis (abnormal backward curvature of the spine), excess lordosis (abnormal forward curvature of the spine), spondylolisthesis (forward displacement of a lumbar vertebra) and other disorders, such as ruptured or slipped discs, broken or fractured vertebrae and the like. Patients who suffer from such conditions usually experience extreme and debilitating pain. A technique known as spinal fixation uses surgical implants which mechanically immobilize areas of the spine assisting the eventual fusion of the treated vertebrae. Such techniques have been used effectively to treat the above-described conditions and, in most cases, successfully elevate the pain suffered by the patient.

One technique for spinal fixation includes the immobilization of the spine by the use of a pair of spine rods that run generally parallel to the spine. In practicing this technique, bone screws are first fastened to the pedicles of the appropriate vertebrae or to the sacrum and act as anchor points for the spine rods. The bone screws are generally placed two per vertebra, one at each pedicle on either side of the spinous process. Clamp assemblies join the spine rods to the screws. The spine rods are generally custom-bent to achieve the desired curvature of the spinal column. Examples of such spinal fixation devices can be found in U.S. Pat. Nos. 4,653,481 and 5,030,220, which are hereby fully incorporated herein by reference. These types of systems are very stable but require implanting screws into each vertebra over the area to be treated. Also, since the pedicles of vertebrae above L2 are relatively small, only small screws can be used. To stabilize the implanted system sufficiently, one vertebra above and one vertebra below the area to be treated are often used for implanting pedicle screws. Proper insertions of screws into the pedicles is time consuming and tedious. If a screw is not inserted centrally in the pedicle and parallel to the axis of the pedicle, an unstable connection may result. Further, if the screw is directed toward the caudal (bottom) side of a vertebra, the screw may impinge on a spinal nerve.

Other fixation systems use hooks which fasten a spine rod to a vertebra for tension (distraction) or compression. The hook systems which are currently in use attach to the vertebral lamina located between the spinous process and the transverse process (such as that described in U.S. Pat. No. 5,005,562) or to the transverse process (such as that described in U.S. Pat. No. 4,269,178) of the vertebra. These types of locations for attachment of the hooks place load onto parts of the vertebra which lead to the possibility of damage to the vertebra and failure of the system during use.

It is desirable that a fixation device be provided which not only reduces the need to implant pedicle screws into the vertebra but also which connects to the strong sections of the vertebra thus reducing the damage to the vertebra after installation of the fixation system. Preferably, the point of attachment of such a fixation device is to a central portion of the lamina or the intersection of the lamina and the spinous process of the vertebra in the area of the spine to be treated. This area has proven to be the strongest bone structure of the vertebra. It is further desirable to provide various configurations of fixation systems to accommodate the various shapes and sizes of vertebrae, and to provide a method and tools for implanting fixation systems. Such improvements translate directly into shorter surgeries and reduced surgical costs.

SUMMARY OF THE INVENTION

The present invention relates to a spinal fixation system which uses grapple hooks to attach to the lamina region of a vertebrae. The grapple hook system comprises a lower hook attached to the lamina on the caudal-side of a vertebra and an upper hook attached to the lamina on the cranial-side of a vertebra. Means are provided for attaching the lower hook to the upper hook to thereby attach the lower and upper hooks to the vertebra and for attaching the lower and upper hooks to spine rods. Spine rods attached to the grapple hook system are placed adjacent the center-line of the spine, on either side of the spinous process of the vertebra.

BRIEF DESCRIPTION OF THE DRAWINGS

Features, aspects and advantages of the invention will be more fully understood when considered with respect to the following detailed description, appended claims and accompanying drawings wherein:

FIG. 1 is a perspective view, looking down the spine from left to right toward the sacrum, of a first embodiment of the present invention;

FIG. 2 is an exploded perspective view of the components of an embodiment of the present invention;

FIG. 3 is a front plan view of a lower hook of the embodiment of FIG. 2;

FIG. 4 is top plan view taken along lines 4—4 of FIG. 3;

FIG. 5 is a side plan view taken along lines 5—5 of FIG. 3;

FIG. 9 is an exploded perspective view of the components of the embodiment of FIG. 8 for fitting to the right side of the spine;

FIG. 11 is a perspective view of an upper hook of the embodiment of FIG. 9;

FIG. 12 is a front plan view of a lower hook of the embodiment of FIG. 9;

FIG. 13 is a partial cross-sectional side plan view taken along lines 13—13 of FIG. 12;

FIG. 14 is a side view of a clamp bolt;

FIG. 19 is an exploded perspective view of an alternate configuration for a spinal fixation system according to the present invention;

FIG. 20 is a partial cross-sectional view of a catch of a lower hook of the system of FIG. 19;

FIG. 21 is an exploded perspective view of another alternate configuration for a spinal fixation system according to the present invention;

FIG. 22 is a side view of a catch of a lower hook of the system of FIG. 21;

FIG. 23 is a partial front view of a lower hook of the system of FIG. 21;

FIG. 25 is an exploded perspective view of a further alternate configuration for a spinal fixation system having one spine rod clamp on a lower hook;

FIG. 26A is a perspective view of a lower hook with a spine rod receiving channel positioned outside of a clamp bolt receiving threaded aperture;

FIG. 26 is a plan view of a still further alternate configuration for a spinal fixation system having a single centrally located hex bolt for a securing means;

FIG. 30 is a perspective illustration of forceps used to hold and crimp a C-spacer onto a shaft of a hex bolt;

FIG. 31 is a perspective illustration of a combination wrench used to tighten the hex bolts;

FIG. 32 is a plan view of a clamp tool used to hold a lower hook;

FIG. 33 is an end view of the clamp tool of FIG. 32;

FIG. 34 is a plan view of a two-prong tool used to hold an upper hook;

FIG. 35 is a plan view of a hex bolt driver;

FIG. 36 is a plan view of a measuring end of a measuring scale;

FIG. 37 is a plan view of forceps used to hold and crimp C-spacers onto shafts of hex bolts; and FIG. 38 is a plan view of a combination wrench used to quickly tighten the hex bolts.

DETAILED DESCRIPTION

Figure 6:
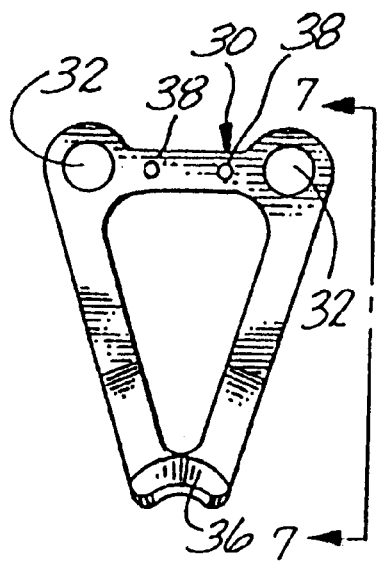
FIG. 6 is a front plan view of an upper hook of the embodiment of the FIG. 2.
Figure 7:
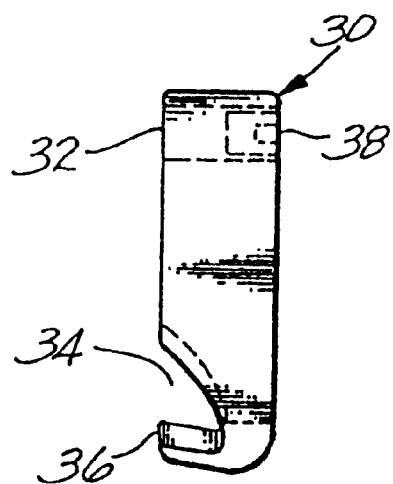
FIG. 7 is a side plan view taken along lines 7—7 of FIG. 6.

The present invention relates to a spinal fixation system which uses a lamina/spinous process hook (also referred to as a grapple hook) connector for use in attaching spine rods to vertebrae for treating various spinal disorders. When the components of the present invention are attached to the area of the spine to be treated, the rods are located close to the spinous process of the vertebrae, i.e., adjacent the centerline of the vertebrae.

One embodiment of the present invention is illustrated in FIGS. 1 to 7. FIG. 1 illustrates a cross brace 4, pedicle screw 6, and the assembled grapple hook system 8 attached to a vertebra of the spine. The system can be used in conjunction with pedicle screws as shown. The grapple hook system (see FIG. 2) comprises a lower hook 10 which attaches to the caudal-side of the vertebra (see FIG. 1). As shown in FIG. 2, an upper hook 30 attaches to the superior side of the vertebra opposite the lower hook and is attached to the lower hook by hex head bolts 50. The hex bolts, when installed, are locked in place by lock washers 70. C-spacers 90 that fit over the major diameter of the threaded section 52 of the hex bolt 50 are used to space the lower hook from the upper hook to prevent crushing of and damage to the vertebra when the system is tightened down to complete final assembly. These components attach the hook system to the spinous process region of the vertebral lamina.

The hook system is also attached to points along the length of a pair of spine rods 92, such as at one end of the rods (see FIG. 1), by clamping top clamps 100 to the lower hook with clamp bolts 120. Other points along the length of the spine rods may then be attached to other vertebrae by conventional clamping systems such as those described in U.S. Pat. No. 5,030,220 or by additional grapple hook systems like those of the present invention. The hook system can also be used to attach only one rod if desired. The components of the grapple hook system are described in detail below.

The lower hook 10, as illustrated in FIGS. 3 to 5, comprise a three armed member. The first arm 12 is, when viewed from its front face (see FIG. 3), generally an inverted triangular shape which includes a hook or catch 14 at its apex. When installed, the hook is placed on the caudal (inferior) side of the vertebra. A face 16 of the first arm abuts against the spinous process of the vertebra, as illustrated in FIG. 1. At an upper end of the first arm (the base of the triangle shown in FIG. 3), and extending out from the first arm on opposite sides, are second and third arms 18. The top of the first arm 12, i.e., the base of the triangle, has a recess 22 to provide clearance for the end of the spinous process when the lower hook is installed.

The second and third arms are mirror images of each other and extend from the first arm at an angle α of approximately 70° from a centerline 23 of the first arm. At the junctions of the second and third arms with the first arm are threaded apertures 20 extending through the lower hook perpendicular to the arms. The threaded apertures receive hex bolts 50 (FIG. 2) to attach the lower hook to the upper hook. The generally cylindrical extended portions 19 of the lower hook, defining the threaded apertures 20, extend outwardly from the body of the lower hook in the same direction as the hook 14 (FIG. 2). The extended portions 19 of the lower hook provide spacing between the lower hook and the upper hook, when the grapple hook assembly is installed, and extend on opposite sides of the spinous process.

When viewed from the top, the lower hook is generally oval shaped with the second and third arms forming the ends of the oval and the first arm at the center of the oval (FIG. 4). On one side of the lower hook, in the middle of the oval above the hook 14, and between apertures 20, is a groove 29 for providing clearance for the spinous process. The groove of the present embodiment allows attachment of the system to the center of the lamina without altering or removing the spinous process. The depth of the groove is varied to provide secure attachment to any vertebra.

At each end of the oval, i.e., each end of the second and third arms, opposite the ends attached to the first arm, are threaded apertures 24 for receiving clamp bolts 120 (see FIGS. 1, 2, and 14) and for attaching top clamps 100 to the lower hook. Between apertures 20 and apertures 24 are channels 26, which are generally half cylinders, extending across the top surfaces of the second and third arms for receiving spine rods 92. The channels include serrations, indicated at 28, for mating with and gripping serrations which run along the length of the generally linear spine support rods.

Referring again to FIG. 2, the top clamps 100 are provided for use in the present invention for attaching the spine rods to the lower hook. Each top clamp has a channel 108 which mates with the channel 26 of the lower hook to define openings or rod receiving apertures for receiving the spine rods 92. The clamp bolts 120 are used to attach the top clamp to the lower hook to securely grip the rods.

The top clamps comprise a roughly cylindrical body with an aperture 110 through the center of the cylinder. The internal diameter of aperture 110 is countersunk so that the head of the clamp bolt is recessed into the aperture after assembly. Between the clamp bolt head 126 and the threaded section 124, is the unthreaded tapered midsection 122 where the diameter of the clamp bolt is intermediate that of the head and the threaded shaft and is sized such that the clamp bolt midsection will fit into the stepped region 102 of the top clamp. The taper 122 provides strength to the top clamp and inhibits breakage. At the upper end of the clamp bolt is a larger-diameter head 126. The larger-diameter portion is sized so that it will slide into the stepped region 104 of the top clamp with the face 123 abutting the face 103 thus holding the top clamp and the lower hook securely on the spine rod when the clamp bolt is screwed in place. The stepped interior of the top clamp allows a distribution of the force conferred by the clamp bolt on the top clamp over a relatively larger area of the top clamp. A lower section 102 of the aperture has a diameter and is tapered such that, when the clamp bolt is attached to the top clamp, a tapered section 122 of the clamp bolt will provide clearance for the taper of the lower section 102. The tapers of the clamp bolt and lower section prevent the clamp bolt from intruding into the channel 108 of the top clamp, and therefore, the length of the arms 18 is kept small. The clamp bolt 120 loads its flange face 123 against the shoulder load face 103 of the countersink in top clamp 100. The countersink 104 is greater in diameter than the diameter of the lower section and is dimensioned so that it can receive the head 126 of the clamp bolt.

The top clamps also each include an arm 106, projecting from the cylindrical body of top clamp, in which is located the channel 108. The channel is serrated, as indicated at 112, for mating and gripping the serrated spine rod. When assembled, the serrated surfaces of the channels of the top clamps and the channels of the lower hook are in facing relation to each other and form the rod receiving apertures in which the serrated spine rods are firmly gripped.

The clamp bolts 120 (see FIG. 2) are used to hold the lower hook and top clamps together and to ensure a firm grip on the spine rod. The clamp bolts 120 have a threaded section 124 to mate with the threaded aperture 24 of the lower hook.

The top face 128 of the clamp bolt includes four notches 130 extending radially from the center to the edge of the top face and spaced at equal distances from each other. The notches align with prongs of a driver so that the surgeon can more easily tighten the clamp bolt and top clamp to the lower hook. A driver and "T" handle are illustrated in FIGS. 15 to 18. The handle 150 comprises a shaft 152. At a first end of the shaft is a handle 154 which is perpendicular to the shaft. At a second end of the shaft is a square shaped attachment site 156. In one side of the attachment site is a spring-loaded ball detent 158. The attachment site 156 of the handle 150 fits into driver 160. The driver comprises a shaft 162. At a first end of the shaft is a square shaped recess 164 for mating with the square shaped attachment site 156 of the handle. Located in opposite sides of the square are recesses 164 for mating with the spring-loaded ball detent 158 to secure the driver to the handle. Located within recess 164 are chamfers 167 which allow depression of spring loaded ball detent 158. The spring loaded ball detent catches in indents 165 to secure the driver to the handle. At a second end of the driver are four prongs 166 for mating with the radial notches 130 of the clamp bolt 120. In use, the handle is fitted into the driver and the prongs of the driver are mated with the radial notches of the clamp bolts 120. The handle is then rotated to tighten or loosen the clamp bolts as required.

The upper hook comprises a member which is generally triangular shaped with an open center when viewed from its front face (see FIGS. 1 and 6). At the two corners of the base of the triangle, are apertures 32 for receiving hex head bolts 50 for attaching the upper hook to the lower hook, and drawing the hooks together onto the vertebra. When viewed from the side (see FIG. 7) the upper hook is generally rectangular shaped with a "cut out" section 34 at the bottom, or apex of the triangle. The cut out section forms the hook 36 for attaching the upper hook to a vertebra. In one embodiment of the present invention blind apertures or recesses 38 are located, adjacent to each aperture 32, on the front face portion of the triangle between the apertures 32 (see FIGS. 6 and 7).

The upper hook is attached to the lower hook by hex bolts 50. The hex bolts include threaded section 52 and head 54 (FIG. 2). Included around the side surface of head 54 are four recesses 56, spaced equal distance from each other around the perimeter of the head.

A locking assembly comprising a locking washer 70 is provided to lock each hex bolt in place when the grapple hook assembly is installed. The locking washer comprises at least two tangs 72 and 74. In use, one of the tangs 72 is deformed into the blind aperture 38 on the upper hook. The hex bolt 50 is threaded into aperture 32 and tightened. The remaining tang 74 is deformed against one of the hex surfaces 54 and alternatively into a recess 56 on the head of bolt 50. When the tang 72 is deformed it locks the bolt in place and prevents it from loosening after installation. In some cases, the recesses 56 are used for wiring to further stabilize and assist in the installation of the fixation system. Preferably, the tangs 72 and 74 are deformed, to the position shown in FIG. 10 prior to use. Thus, there is no need to bend tang 72 at all and tang 74 need only be bent slightly farther upward to engage the head of the bolt 50. With the tang 74 prebent, it is easier to grip the tang and bend it into its final position. This does not make assembly any more difficult. A washer tang must be aligned with the recess 38 whether or not the tangs are prebent. Prebending the tangs actually makes it easier to assemble because the tangs 72 will prevent the washers from rotating out of position while the hex bolt 50 is being tightened. It is further preferred that the tangs 72 be prebent and of a size so that they are press fit into the blind aperture during the manufacturing process. Press fitting the tang 72 into the blind aperture both fixes the lock washer form rotation and secures it to the hook.

In use, the lower hook is placed on the caudal side of a vertebra adjacent to the area of the spine to be treated. The upper hook is then positioned in facing relation to the lower hook on the other side (cranial/cephalad) of the vertebra (see FIG. 1). The hex bolts 50 are inserted through the apertures 32, threaded into the apertures 20, and tightened until the lamina is securely grasped. The gap between the lower hook and upper hook is measured, and appropriately sized C-spacers 90 are installed between the aperture faces 20 and 32 of the lower and upper hooks respectively and crimped onto the threads 52 of the hex bolt. Sizes of the C-spacers are varied as needed to correctly distance the lower and upper hooks to fit around the lamina of the vertebra to be treated. Thus, the lower and upper hooks are secured to the vertebra. The tangs 74 are deformed into the recesses 56 or against the hex head flats 54 on the head of the hex bolt to prevent rotation and loosening of the hex bolt after installation.

Spine rods 92 are placed in the channels 26 of the lower hook and clamp bolts 120 are then inserted through aperture 110 of the top clamp and threaded into the aperture 24 of the lower hook, using the driver, illustrated in FIGS. 15 to 18 and described above. The prongs of the driver are mated with the notches of the clamp bolt and the driver is then used to tighten the clamp bolt into the top clamp, thereby securing the spine rod to the lower hook. The clamp bolt, when tightened, is contained within section 104 of the top clamp, leaving exposed a small portion of the inner upper edge of wall 114 of the top clamp.

After the clamp bolt is in place, an upper portion of the wall 114 is crimped or deformed inwardly at least at one point along its periphery corresponding to one of the radial notches. The crimp ensures that the clamp bolt is firmly locked in place and that undesired rotation of the clamp bolt is inhibited once the system is installed.

In the event that some adjustment, and hence removal of the clamp bolt is necessary, the crimp is easily overcome when the clamp bolt is unscrewed to release the top clamp by using the driver to remove the clamp bolt. After any required adjustments have been made, the screw-and-clamp assembly is secured in place (re-crimped), as described above.

The other ends of spine rods 92 can then by attached to conventional clamps, such as those described in U.S. Pat. Nos. 4,653,481 and 5,030,220, or other grapple hook assemblies which are placed on the opposite side of the attachment site of the described grapple hook of the area of the spine to be treated. Clamping of the spine rods thereby stabilizes the region of the spine to be treated.

Another embodiment of the present invention is illustrated in FIGS. 8 to 13. This embodiment of the invention allows the surgeon to clamp only one side of the spine with each clamp (unilateral attachment) where damage to the spinous process occurs as a result of the surgery or the initial injury or condition. The grapple hook system of this embodiment is similar to that described above, except that two sets of components are installed on a vertebra, that is one on each side of the spinous process. Thus, the spinous process is not encircled. In FIG. 9, the clamps for fitting to the patient's left side of the spine are shown. The components for fitting to the patient's right side of the spine are mirror-images of these components. Because the components of this embodiment of the present invention are similar to the embodiment described above, similar part numbers are used for similar parts.

This embodiment of the present invention comprises a lower hook 10 which attaches to one side of a vertebra lamina, on one side of the spinous process. An upper hook 30 is attached to the lamina of the vertebra opposite the lower hook and on the same side of the spinous process, and the upper hook is attached to the lower hook by a hex bolt 50. The hex bolt, when installed, is locked in place by the lock washer 70. Again, a C-spacer 90 that fits over and is later collapsed on the major diameter of the hex bolt is used to space the lower hook from the upper hook to prevent crushing of and damage to the lamina when the system is installed.

These components attach the hook system to the lamina region of the vertebra. The hook system is also attached to a point along the length of a spine rod 92, such as at one end of the spine rod (see FIG. 8), by clamping the top clamp 100 to the lower hook with the clamp bolt 120. Another point along the length of the spine rod, such as its other end, can then be attached to other vertebra by conventional clamping systems or by grapple hook clamping systems according to the present invention. The components of this embodiment of the grapple hook system are described in detail below.

Figure 8:
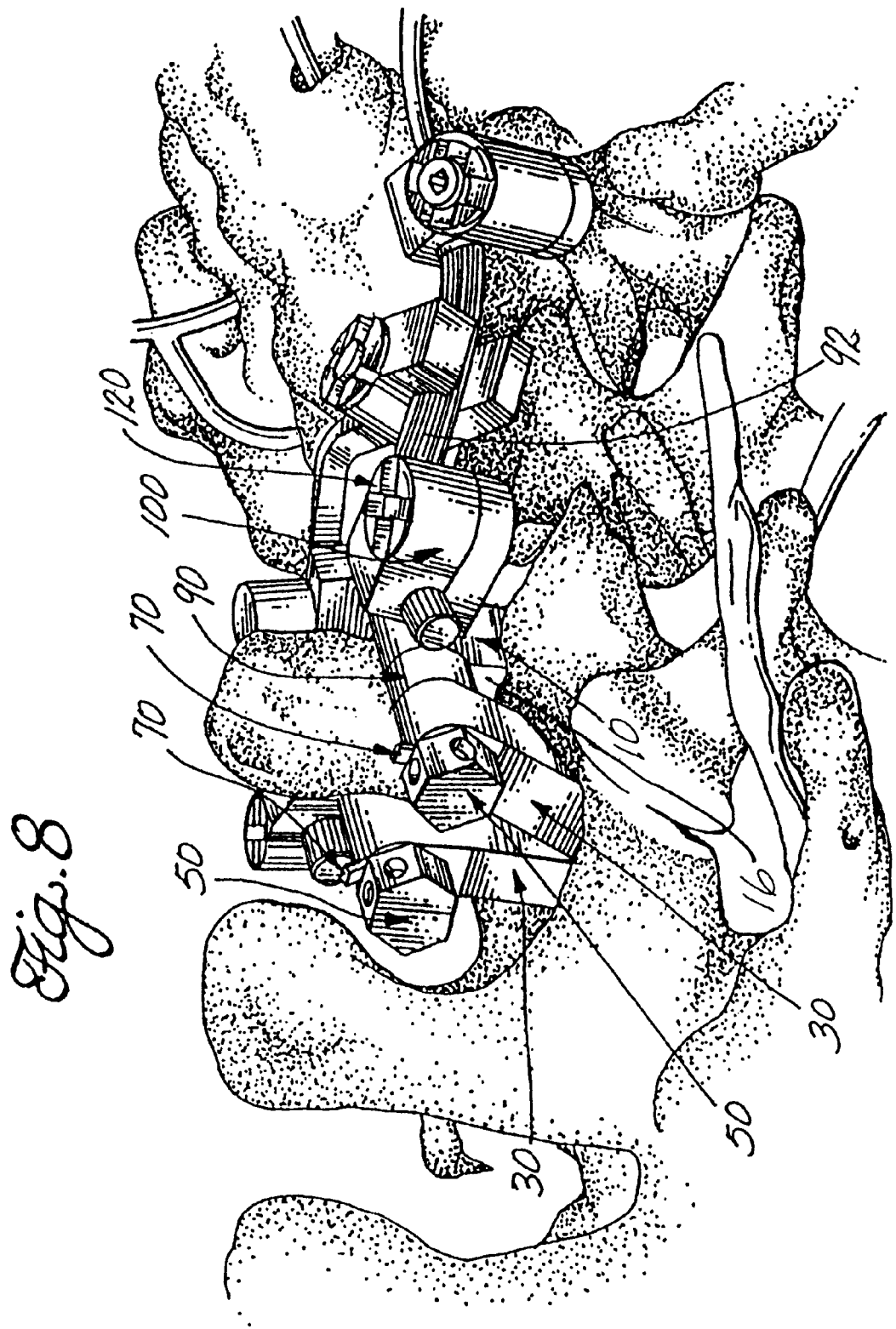
FIG. 8 is a 45° lateral perspective view, looking down the spine from left to right toward the sacrum, of another embodiment of the present invention attached to a vertebra.
Figure 15:
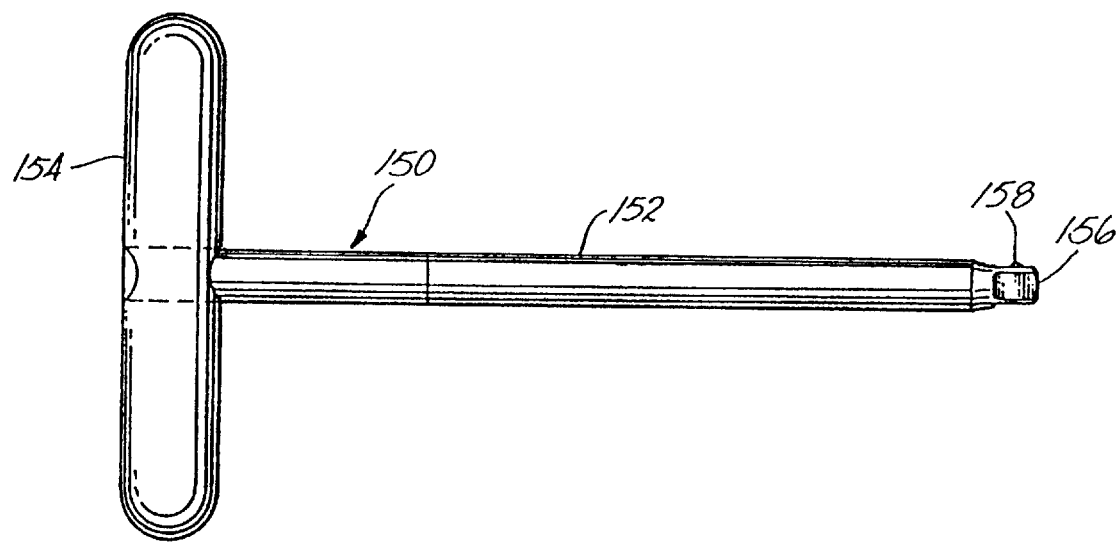
FIG. 15 is a side view of a "T" wrench handle for use in the present invention.
Figure 16:
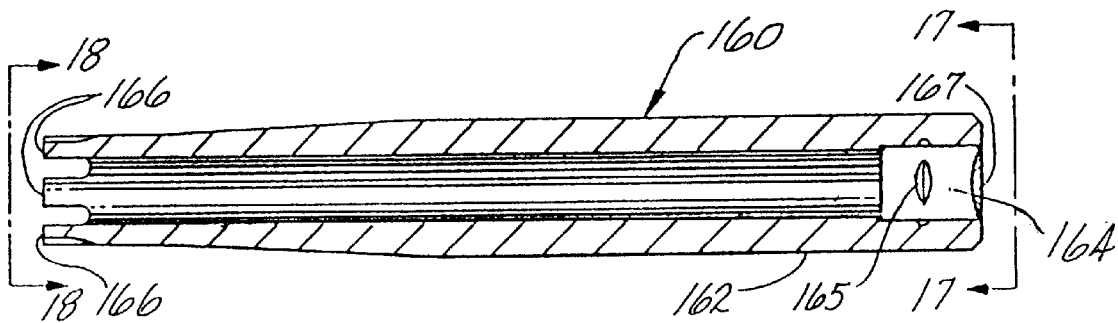
FIG. 16 is a partial cross-sectional side view of a driver for use in the present invention.
Figure 17:
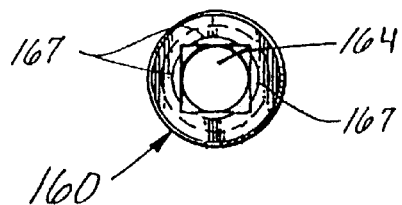
FIG. 17 is a bottom view of the driver taken along line 17—17 of FIG. 16.
Figure 18:
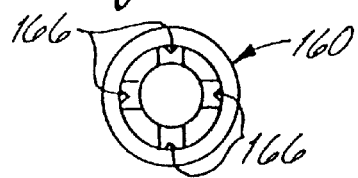
FIG. 18 is a bottom view of the driver taken along line 18—18 of FIG. 16.

The lower hook 10, as illustrated in FIGS. 12 and 13, is an L-shaped member, when viewed from the front face (see FIG. 12). One arm 12 of the "L" includes a hook or catch 14 at its end that is configured to grip the lamina region of a vertebra on the sacrum/caudal side of the vertebra. A mirror image of hook 14 illustrated in FIG. 12 grips the lamina region of the vertebra to the patient's right of the spine, as illustrated in FIG. 9 looking down the spine toward the sacrum. A second lower hook, identical to the lower hook 10 shown in FIG. 9, except that it is its mirror image, is attached to the patient's right side of the spine, as illustrated in FIG. 8. When installed, the hook is placed on the caudal side of the lamina. The face 16 of the "L" above hook 14 abuts the caudal edge of the lamina of the vertebra, as illustrated in FIG. 8. On the other arm 18 of the "L" has a threaded aperture 24 for receiving the clamp bolt 120 and attaching top clamp 100 to the lower hook (FIG. 9). Adjacent to and extending perpendicular to aperture 24 across the top surface of lower hook 10 is located a channel 26 for receiving the spine rod 92. The channel includes serrations, shown at 28, for mating and gripping the spine rod which includes serrations along its length. At the junction of the arms of the "L" and extending generally parallel to channel 26 is a threaded aperture 20 for receiving the hex bolt 50 and attaching the lower hook to the upper hook.

Figure 10:
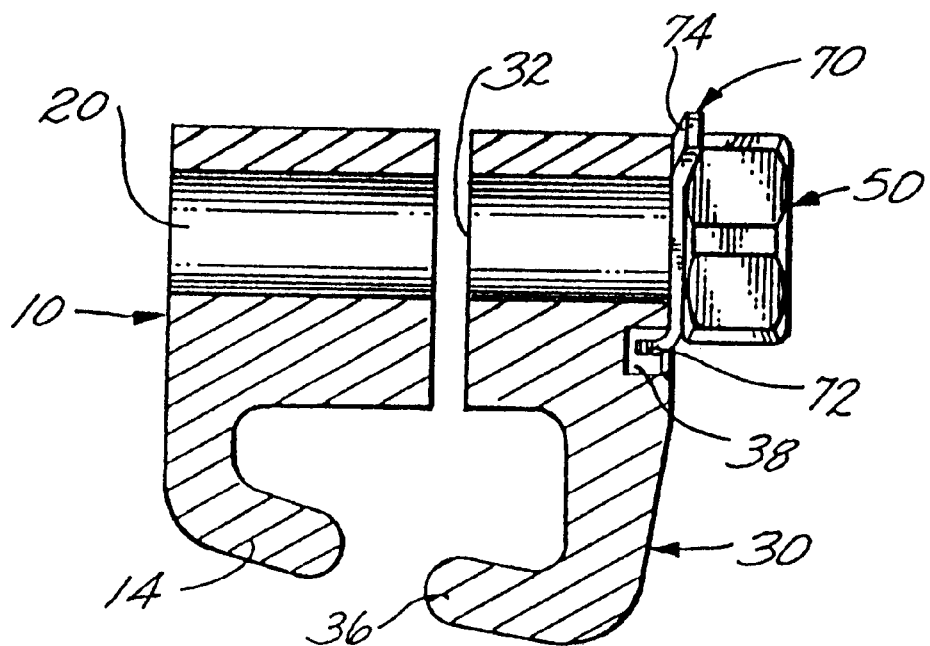
FIG. 10 is a partial cross-sectional side view of the upper and lower hooks of FIGS. 11 to 13 shown in an assembled orientation.

The upper hook 30 (see FIG. 11) when installed mates with the lower hook described above by gripping the lamina region of a vertebra on the cranial-side of the vertebra (see FIGS. 8 and 10). A second upper hook which is identical, except it is its mirror image, is used to mate with the lower hook placed on the same side of the spine. The upper hook comprises a member with an aperture 32 extending through the top of the upper hook, for receiving the hex bolt 50 to attach the upper hook to the lower hook with the vertebra lamina therebetween. A blind aperture or recess 38 is located on the surface of the upper hook adjacent to one opening of the aperture 32. A hook 36 extends away from the section of the upper hook which includes the aperture 32. The hook 36 projects from the body of the upper hook in a direction opposite the surface containing the recess 38 and the lock washer 70. The section which includes the hook, is off-set from the aperture, such that when the bottom of the hook is held in a horizontal position the aperture is not directly above the hook, but offset to one side. For attaching to the right side of the vertebra (see FIG. 8), aperture 32 is offset to the right relative to the hook. For attaching to the left side of the vertebra (see FIG. 8), aperture 32 is offset to the left relative to the hook. In FIG. 8, the hex bolt 50 is inserted through the aperture 32. Thus, the position of the bolt is horizontally offset from the hook 36 when the hook 36 is horizontal. This offset allows the upper hook to be placed at the lamina of the vertebra but avoids contact with the spinous process. Further, the upper hook is attached to the lower hook by the hex bolt 50 as described above for previous embodiments.

In use, a lower hook is placed on the caudal side of the lamina and on one side of the spinous process. The upper hook is then positioned in facing relation to the lower hook on the other side (cranial) of the lamina and on the same side of the spinous process, as illustrated in FIG. 8. The hex bolt 50 is inserted through the aperture 32, threaded into the aperture 20, and finger tightened. The C-spacer 90 is installed between the face of the aperture 20 of the lower hook and the face of the aperture 32 of the upper hook, and then the C-spacer is crimped (collapsed) in place. The size of the C-spacer may be varied as needed to correctly distance the lower and upper hooks to fit around the lamina to be treated. Thus, the lower and upper hooks are secured to the vertebra.

A spine rod is placed in the channels of the lower hook, and the clamp bolt 120 is then inserted through aperture 110 of the top clamp and threaded into the aperture 24 of the lower hook, as described above for the first embodiment.

The assembly process is then repeated to attach a second grapple hook assembly to the other side of the spinous process, on the same vertebra.

The components of the grapple hook of the present invention are preferably made of an alloy capable of resisting corrosion when installed in a human body. It has been found that 316 stainless steel which has been electropolished and passivated to resist corrosion works well. Other metal alloys, such as titanium or alloys of titanium also may be used.

Recognizing that the features, size for example, of each vertebra in a patient's spine are different to some degree, and that the corresponding vertebra of different patients have different features, it is desirable to have a variety of fixation system configurations with varied features and size to obtain satisfactorily secure clamping on any vertebra of any patient. The configuration of the fixation system illustrated in FIG. 2 is a basic configuration designed for the upper lumbar and lower thoracic vertebrae: L3, L2, L1, T12, T11, and T10. The features of the FIG. 2 configuration are varied as described below with respect to an alternate configuration. However, some vertebrae are too large and shaped so that substantial changes in features are necessary. To that end, alternate fixation system configurations of the embodiment shown in FIGS. 2–7 designed for specific vertebra are illustrated in FIGS. 19 through 26. These alternate configurations operate in substantially the same way as previously described with respect to the embodiment of FIGS. 2–7, and though the alternate basic configurations are intended for specific regions of the spine, there is some over lap especially in large or small patients. Thus, the alternate configurations have hex bolts 50 for attaching lower hooks to upper hooks with C-spacers 90 interposed between the hooks to prevent crushing the lamina and have lock washers 70 with tangs 74 for locking the hex bolts 50 from rotation. Further, the clamp bolts 120 secure the top clamps 100 to the arms 18 of the lower hooks to form the spine rod receiving areas with the channels 26, 108 of the lower hook arms 18 and the top clamps 100 respectively.

The alternate configuration, generally designated 200 and shown in FIG. 19, is a basic configuration designed especially for the typical L4 and L5 lumbar vertebrae. The L4 and L5 lumbar vertebrae are large and typically have generally horizontal laminas while the patient is lying prone. To obtain a satisfactory fit on these large vertebrae, the upper hook, generally designated 204, has longer arms 206 extending away from the threaded apertures 208 which receive the hex bolts 50. The longer arms allow for a thicker lamina. A thicker lamina means a longer distance between the posterior side of the lamina and the vertebral foramen in which the hook catches, and thus, the thicker lamina requires an upper hook 204 with an increased distance from the hex bolts 50 to the upper catch 210. The upper catch 210 has an outer surface 212 with an outer radius and an inner surface 214 with an inner radius which is larger than the outer radius. The inner radius of this embodiment is larger than for other embodiments so that it can mate with the relatively large inner radius of the central lamina wall facing the vertebral foramen of large vertebrae. The inner radius 212 which faces the vertebral foramen and hence the spinal cord is selected to provide a sufficiently thick upper catch having the required strength but thin enough so that the spinal cord and other contents of the vertebral foramen are not hindered. Further, the inner and outer radii do not need to be concentric. Additionally the contours of the inner and outer surfaces are varied.

The width W and depth D of the upper catch are sized to mate with the lamina. The cylindrical portions 216 of the upper hook 204 have a larger height H and may be spaced farther apart. The larger height reduces the length of the gap between the lower and upper hooks so that a standard size range of C-spacers 90, so named because of their C-shaped cross section, can be used. The standard size range is from 1 mm to 9 mm with a different sized C-spacer at every 0.5 mm increment. Occasionally the gaps between the upper and lower hooks are larger than 9 mm. If, for example, the gap is 10 mm, two 5 mm spacers can be used in combination to fill the gap. Other length combinations such as 3 mm and 7 mm could be utilized. The hex bolts are also provided in different lengths to accommodate different vertebra sizes. The preferred lengths are 20 mm, 25 mm, and 30 mm. Because the C-spacers are crimped onto the threaded portion of the hex bolt and tightened between the upper and lower hooks by the hex bolt, there is no danger of them becoming loose and detaching from the fixation system. The posterior side lamina mating angle α of the arms extending to the catch is also sized to mate with the posterior wall of the lamina. Further, the degree at which the catch extends away from the arm can be varied for engagement of the vertebral foramen wall of the lamina. The lamina mating angle α and the catch are designed to ensure that the upper hook minimally protrudes into the vertebral foramen when the hook is attached to the vertebra. The angle α also ensures that the catch of the upper hook is as close as possible to the spinous process when installed. The taper angle γ, which determines how abruptly the upper hook narrows moving toward the catch, is set so that the hook fits in between the inferior particular processes of the vertebra above the attachment vertebra.

The lower hook, generally designated 202, has a thick catch 218 with an inner surface 220 contour having a centrally located groove 222 to mate with a central ridge on the caudal side of the vertebral foramen wall of the lamina. The contour can be adjusted to make the groove deeper or more shallow. The outer surface 224 of the catch is generally flat, but the contour can be modified to include a radius similar to that in the upper hook to avoid hindering the contents of the vertebral foramen. As with the upper catch, the width and depth of the upper catch are varied from system to system to obtain a variety of configurations. The central portion of the lower hook has an opening 226 and a cross member 228 extending between the cylindrical portions 230 which define the apertures 232 for receiving the hex bolts 50. The height of the cylindrical portions is varied and can extend beyond the body of the lower hook as the cylindrical portion 19 does in the previous embodiment (FIG. 4). The cross member extends across the groove 29 of the previous embodiment and increases the strength of the system. As with the upper hook the distance between the cylindrical portions is varied. In this embodiment, the length of the cross member is varied to correspond to the distance between the cylindrical portions.

Referring to FIG. 20, the catch angle β between the inner surface 222 of the catch and the centerline 234 of the apertures 232 extending through the cylindrical portion 230 of the hook is approximately 32° in the embodiment illustrated. The catch angle β, illustrated between the catch and the edge 236 of the arm, which is parallel to the centerline of the aperture 232, and the distance between the catch and the apertures 232, are also varied from system to system so that a catch with a satisfactory fit for any patient is assured. Another feature which is varied is the distance between the centerline 234 and the beginning of the catch. The greater the distance between the centerline and the catch, the thicker the lamina which the fixation system can clamp on to. The length L of the lower catch is varied. The length is chosen to provide sufficient strength while avoiding hindrance of the contents of the vertebral foramen. Other features which are varied are the distance between the apertures 232 and the channels 26, the length, depth, and width of the arms 18, and the angle of the channel 26 relative to the apertures 232.

Another configuration of a fixation system, generally designated 240, illustrated in FIG. 21 is a basic configuration designed for the cervical and upper thoracic vertebrae: C1–T11. As with the configuration of FIG. 19, the various features of the upper hook, generally designated 242, such as the radii, depth, and width of the catch, the height of the cylindrical portions, spacing between the cylindrical portions, the angle α of the arms extending to the catch, and others are varied to obtain a plurality of system configurations. For example, the cylindrical portions 246 which define the apertures to receive the hex bolts 50, have a smaller height than the configuration of FIG. 19 because the upper thoracic and cervical vertebrae are generally not as large as the lumbar vertebrae.

The lower hook, generally designated 244, also has features which are varied as described above in conjunction with the configuration of FIG. 19: the height of the cylindrical portions 248 (which define the hex bolt 50 receiving apertures 250), the catch angle β of the catch, the length of the catch, and others. Specific to this configuration, the axis of the channels 26, defined by the edge 254 of the channels, are set at an angle δ of approximately 15° relative to a centerline 252 of the apertures 250. This angle δ is varied between systems to accommodate diversely shaped vertebrae. Referring additionally to FIG. 22, the catch angle β' of the catch 256 relative to the outer surface 258 of the catch in this configuration is preferably 15°. The outer surface has a radius of curvature which is varied to avoid hindering the contents of the vertebral foramen. The inner surface 260 of the catch 256 is provided with a groove of variable depth and width 262 to mate with a central ridge on the lamina wall. Referring to FIG. 23, the edges 264 of the catch 256 are rounded to fit securely against the curved vertebral foramen wall of the lamina. The lower hook taper angle ε is approximately 26° in the illustrated configuration. The taper angle ε is varied to assure a satisfactory fit between the inferior articulate processes of any vertebra. Also, the length of the arms 266 extending from the body of the lower hook to the catch is varied to compensate for varying thicknesses of lamina.

In the upper thoracic and cervical vertebrae, the spinous processes typically extend toward the caudal side of the vertebra. The above described configurations would not supply a consistently secure clamp on these vertebrae. Therefore, a large recess 268 is provided between the cylindrical portions 248 allowing the lower clamp to fit around the downward extending spinous process and clamp securely to the lamina. Thus, the face 16 shown in the embodiment of FIG. 3 is essentially eliminated. The bottom surface 270 of the arms 18 can also be tapered in various directions depending on the intended vertebra. In the illustrated configuration, the bottom surface is tapered toward the end 272 of the arm 18 so that the arm gets thinner toward the end 272 thereof. This modification allows the fixation system to, for example, clamp securely to a vertebra with processes that protrude a greater distance in the posterior direction.

Figure 24:
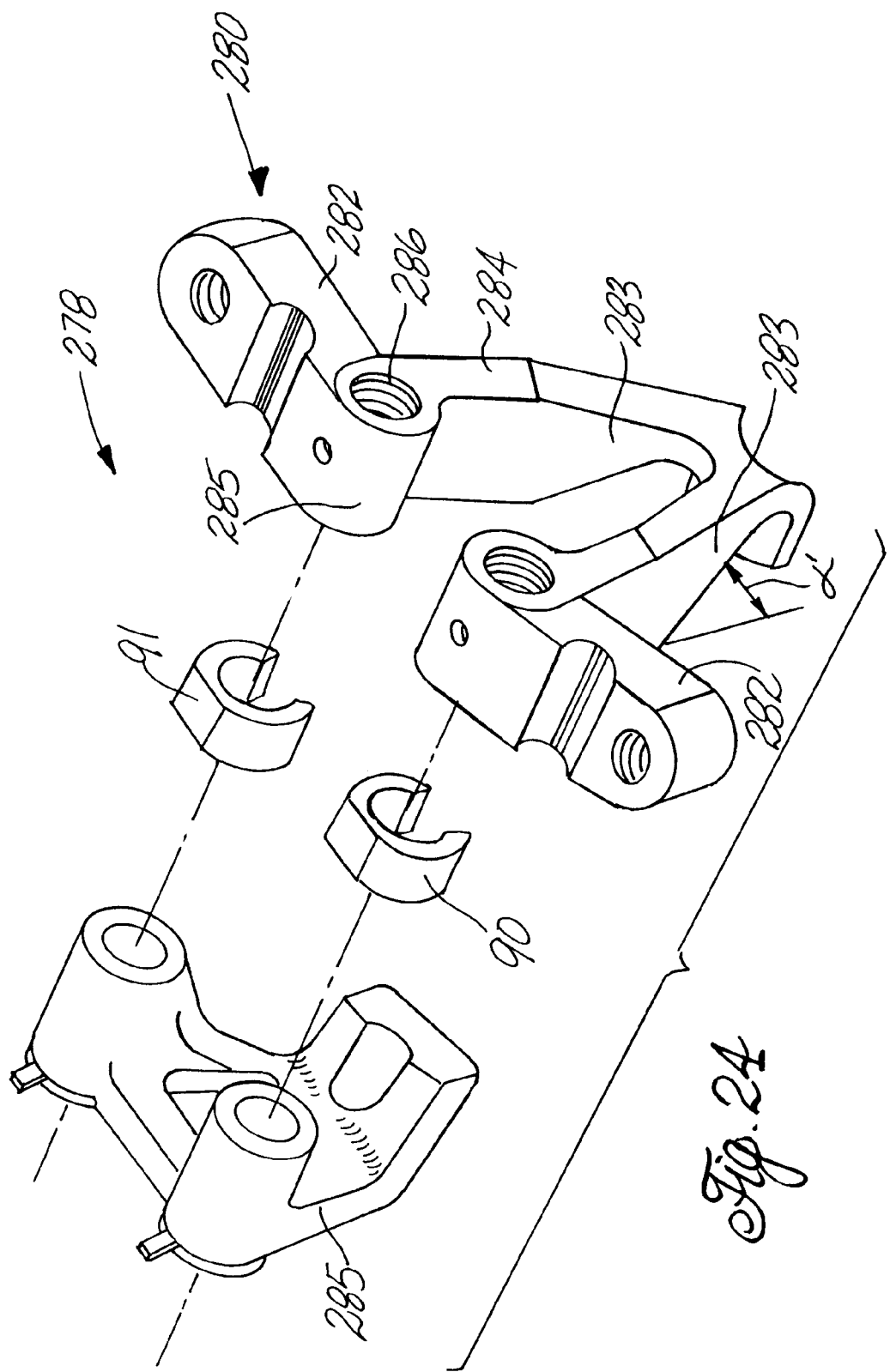
FIG. 24 is an exploded perspective view of still another alternate configuration for a spinal fixation system having a spine rod clamping mechanism on an upper hook and omitting portions of the clamping mechanisms.

The previous embodiments of the fixation system have all provided the spine rod clamping mechanism on the lower hook. Referring to FIG. 24, the fixation system, generally designated 278, has a spine rod clamping mechanism, generally designated 280 provided on the upper hook 284 instead of the lower hook 285. The arms 282 are desirably positioned vertically between the inferior particular processes and the superior particular processes on both sides of the spinous process. This is achieved by providing sufficiently long arms 283 extending to the catch along angle α'. The arms 283 extend to a point between the inferior particular processes and the superior articular processes and allow arms 282 to be attached at the opposite end. This is preferably achieved by angling the arms 282 from the cylindrical portions 285 defining the threaded apertures 286 for receiving hex bolts. The angle of intersection between the arms and the cylindrical portions (the arm intersection angle) is another feature which can be varied from system to system. Another difference between the embodiment of FIG. 2–7 and this embodiment (see also the embodiments of FIGS. 19–23) is that, the hex bolts thread into the upper hook instead of the lower hook, and the washers lock against the lower hook instead of the upper hook.

Other configurations with different locations of the spine rod clamping mechanism are also possible, and for some applications of the invention, as shown in FIG. 25, only one spine rod clamp, generally designated 288, is provided on one side of a fixation system. In this embodiment, one arm 290 extends from the cylindrical portion 292 and includes the channel 26 for receiving the spine rod. One top clamp 100 and one clamp bolt 120 are also provided to hold the spine rod in the spine rod receiving area defined between the channels 26 and 108. The single spine rod clamp can be located on the upper hook 294 or on the lower hook 296 as shown. Further, the single spine rod clamp can be located on either side of the hooks. Two hex bolts 50 are provided to secure the upper hook to the lower hook with a vertebral lamina therebetween, and C-spacers 90 are provided to prevent damage to the vertebral lamina.

Referring to FIG. 26A, the position of the spin rod on the arms 18 can be varied so that it is closer or farther away from the spinous process. To achieve this variation the length of the arms can be modified, and further, the channels 26 can be located outside of the threaded apertures 24 for receiving the clamp bolts.

It is also possible to provide a fixation system as shown in FIG. 26 having only one hex bolt to secure the upper hook to the lower hook. In this embodiment a preferably centrally located cylindrical portion 297 defines a single aperture 298 for receiving a hex bolt 50. Thus, both the means for securing the upper hook to the lower hook and the catches, generally designated 299, are positioned centrally on the lamina for attachment to the vertebra. Again, the spine rod clamping mechanism can be provided on the upper or lower hook, or a single spine rod clamp can be provided on the upper or lower hook. To implant this embodiment of the spinal fixation system it is necessary to remove the spinous process from the vertebra.

A spinal fixation kit includes a plurality of fixation systems having the general features of the upper and lower hooks for the lumber, lower thoracic/upper lumbar, and upper cervical regions as described, but the specific dimensions of these features, such as the radii, depth, and width of the catch, the height of the cylindrical portions, spacing between the cylindrical portions, the angle a of the arms extending to the catch, and others are varied between different systems. Thus, a surgeon can try several hooks until the best fitting hooks for the specific vertebra are found. Having a plurality of fixation systems with a varied combination of features provides a system with a satisfactory fit for each vertebra of any given patient with minimal removal of laminar and process done. Features other than those specifically described can be varied to obtain satisfactory fits.

Figure 27:
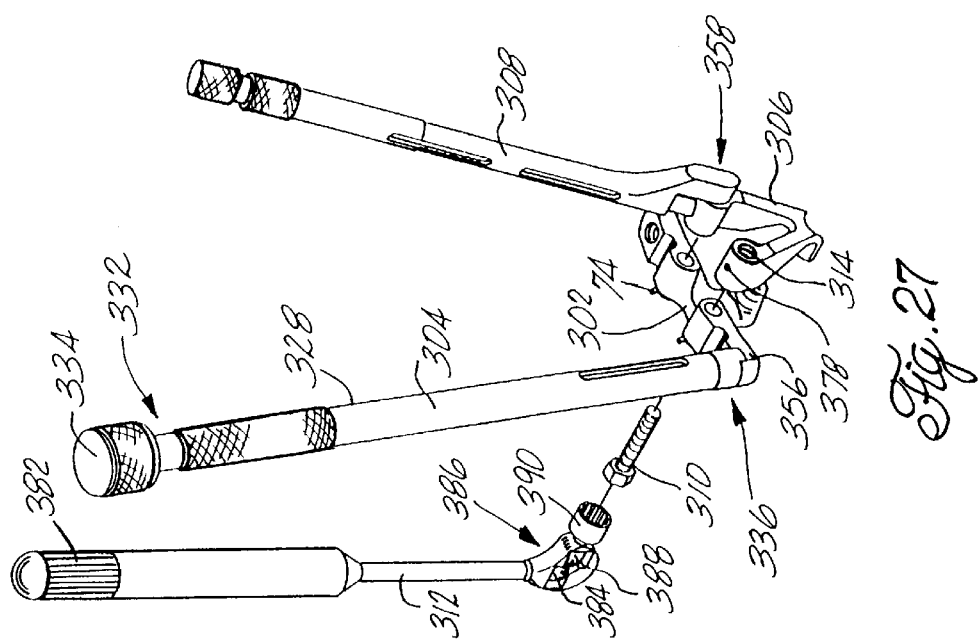
FIG. 27 is a perspective illustration of the assembly of a spinal fixation system illustrating holding of upper and lower hooks with specially designed tools.

The spinal fixation kit and the independent fixation systems are implanted using specially designed tools, shown in FIGS. 27–38, which will be briefly described in conjunction with the method of implanting a fixation system provided in a kit and in more detail below. Referring first to FIG. 27, the lower clamp 302 is held by a clamp tool 304. The surgeon then inserts the lower clamp onto the desired vertebra and checks the fit. If the embodiment of FIG. 26 is utilized, the surgeon must first remove the spinous process. If the fit is not satisfactory, a different lower clamp provided in the kit with features varied as described above is held by the clamp tool 304 and placed into position on the vertebra to check the fit. This process is repeated until a satisfactory fit is achieved. After inserting the lower clamp, an upper hook 306 held by a two prong tool 308 is inserted in the desired vertebra to check the fit. If the fit is not satisfactory, differently configured upper hooks provided in the kit are checked until a satisfactory fit is obtained.

With both the upper and lower hooks in position on the desired vertebra, a surgical assistant holds the two prong tool and the clamp tool so that the apertures are aligned while the surgeon inserts a hex bolt 310 into a hex bolt driver 312 and inserts it into the apertures. After one of the hex bolts is partially threaded into one of the threaded apertures 314 of the upper hook 306, the two-prong tool is preferably removed a shown in FIG. 28, and a second hex bolt 310 is inserted into the hex bolt driver 312 and threaded into the other threaded aperture. The hex bolts are tightened by alternating side to side to avoid binding. The partial assembly should be gently toggled or shifted during tightening to assure the securest possible fit. The hex bolts are then tightened preferably until movement is prohibited. A combination wrench 326 can be used at this point to tighten the hex bolts to a point where movement is eliminated.

Figure 29:
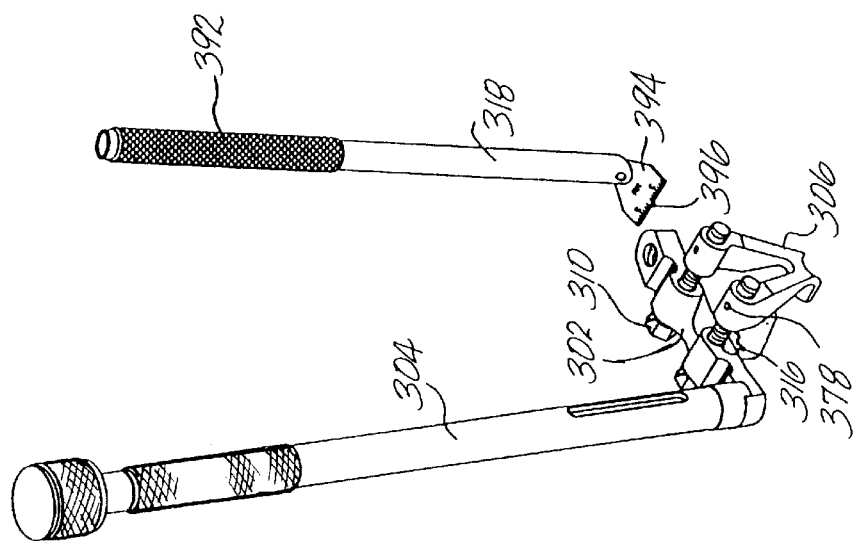
FIG. 29 is a perspective illustration of measuring a gap in the assembly of FIG. 28.
Figure 28:
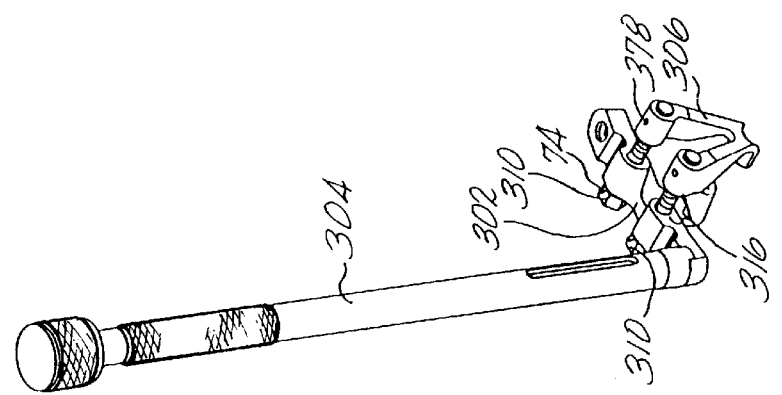
FIG. 28 is a perspective illustration of a partially assembled spinal fixation system with two hex bolts in place.

The gap 316 is measured with a measuring scale 318 shown in FIG. 29. A reading is taken from the measuring scale on both sides of the clamp, and C-spacers 90 of a size corresponding to the measurement is inserted into a spring loaded C-spacer crimping forceps 320 as illustrated in FIG. 30. The slot (opening) 322, which extends over the length of the generally cylindrically shaped body of the C-spacer 90, receives the shaft 324 of the bolt and forceps are squeezed to crimp the C-spacer onto the bolt. The C-spacer is provided with a thin walled portion 91 to allow the spacer to deform for easy crimping (collapsing) onto the bolt. The same size C-spacer is preferably used on both sides. If one gap is smaller than the other, the smallest size is preferably used. To finish tightening the hex bolts, a combination wrench 326 engages the head of the hex bolts as illustrated in FIG. 31 and securely tightens them. To finish tightening, a box wrench provided opposite the open side of the combination wrench is utilized. The surgeon should attempt to gently toggle the assembly again to assure that there is no movement and that there is adequate clamping pressure. Next the clamp hook is removed, and then the tangs 74 of the lock washers 70 are bent into place. With the hooks secured to the vertebra, the spine rods can be clamped to the lower hook as described above.

Turning to a detailed discussion of the tools, FIGS. 32 and 33 show the clamp tool used as described. The clamp tool comprises an outer cylindrical shell 328 enclosing a generally cylindrical inner shaft 330 which terminates at the handle end, generally designated 332, with a knurled knob 334 and at the clamp end, generally designated 336, with a threaded post 338. The inner shaft rotates relative to the shell and translates longitudinally relative thereto between upper and lower anvils 340, 342 respectively which are enlarged diameter portions of the inner shaft. A stop pin 344 is fixed to the outer shell intermediate of the upper and lower anvils and extends across the opening within the shell without passing through the center of the opening. Thus, the inner shaft translates over the distance between the two anvils and rotates without interference from the stop pin. The section of the outer shell near the handle end is provided with a knurled surface 346 to aide gripping the tool.

Referring additionally to FIG. 27, the threaded rod mates with the threaded aperture 348 of the lower hook 302. The threaded rod is threaded into the aperture by turning the knob of the clamp tool. As the rod is threaded in, the upper surface 350 of the lower hook engages the clamp engagement surface 352 of the clamp tool. Flanges 354 attached to the outer shell engage the flat sides 356 of the lower clamp securing it rotationally. Thus, the lower hook 302 is securely held by the clamp tool 304.

Referring to FIG. 34 illustrating the two prong tool, the prong end, generally designated 358, of the inner shaft 360 terminates in a small pin 362. The inner shaft and the outer cylindrical shell 364 are threadably engaged just below the knurled knob 366 at the knurled surface 368 of the outer shell so that the pin can be extended from and retracted into the outer shell. A stop pin 370 is attached to the outer shell extending across the opening of the outer shell without passing through the center of the opening to prevent removal of the inner shaft from the outer shell and allow relative rotation. The outer shell terminates at the prong end with an L-shaped member 372 having a cylindrical pin 374 as its free leg. The small pin and the cylindrical pin intersect at 90°.

Referring additionally to FIG. 27, the cylindrical pin 374 is received into the threaded aperture 314 of the upper hook 306. The small pin 362 is aligned with a securement aperture 378 in the wall of the upper hook and the inner shaft is threaded so that the small pin is extended out of the outer shell and into the securement aperture 378. Thus, the upper hook is securely held. To release either the clamp tool or the two prong tool, the knobs are simply turned to unthread the tools.

The hex driver 312 is shown in FIG. 35. The handle end, generally designated 380, has a rotatable and grooved handle 382 which is rotationally coupled to a parallel drive gear 384 at the drive end, generally designated 386. A transverse drive gear 388 meshes with the parallel drive gear and is rotated thereby. A socket 390 for receiving the heads of hex bolts is rotationally coupled to the transverse drive gear, so that rotation of the handle 382 results in rotation of the socket 388 and tightening or loosening of the hex bolts depending on the direction of rotation. The size of the socket is such that the head of the hex bolt fits snugly therein so that the bolts can be carried in the socket without dropping them.

Referring to FIGS. 29 and 36, the measuring scale has a knurled handle 392 to aide gripping the scale. The actual scale is capable of measuring a gap 316 from 1 to 15 mm inclusive and is located on a plate 394 extending away from the shaft of the scale at an angle. The scale is not an actual measuring device. When the reading is 5 mm, the actual gap is 5.5 mm. Thus, a 5 mm C-spacer can slide into the gap without interference, and the C-spacer will allow approximately 0.5 mm of further tightening. A prong 396 extends from the edge of the plate and is used to engage the edge of either the upper hook or the lower hook. The prong 396 consistently fixes and steadies the scale so that accurate measurements are made.

Referring to FIG. 37, the forceps 320 comprises two handles 398, 400 pivotally attached at 402. Each handle terminates at a handle end, generally designated 404, with a loop 406 to receive fingers. A resilient member 408, preferably a spring, is adjacent to the loops and is interposed between the handles to bias the handles toward each other. At the clamp end, generally designated 410, of the forceps, the handles terminate in claws 412 which define an opening 416 for holding a C-spacer 90 therebetween as shown in FIG. 30. Teeth 414 are provided in the upper portion of the claws. As the spring pulls the handles together, it also pulls the claws together. Thus, the C-spacer is held between the claws without any applied force. With the C-spacer between the claws, the spring is tensioned and the loops are forced apart. After the C-spacer is placed on the shaft 324 of the hex bolt 310, the loops are squeezed together crimping the C-spacer onto the shaft in between the upper and lower hooks.

Referring to FIGS. 31 and 38, the combination wrench has an extended shaft 418 to provide a torque arm for tightening the hex bolts. The shaft terminates at one end with a speed wrench, also referred to as a ratchet or one way wrench head 420. The shaft terminates at the other end with a conventional wrench head of either the box wrench 422 or open-end wrench 424 type. The wrenching heads are preferably angled as is conventional in box wrenches. To allow the ratchet action, one prong 426 of the ratchet(open) head is truncated. When the wrench is turned in the direction prong away from the truncated prong 426, there is no surface to engage the nut, and thus, the wrench slips over the nut. When the wrench is turned in the direction opposite arrow 428, a full prong 430 engages the nut and turns it. Thus, the hex nuts can be tightened with a quick ratchet action. The conventional wrench end is provided to finally tighten the hex bolts. The described method of implantation and the tools used therein substantially reduce the time required for a spinal fixation surgery.

The present invention is not to be limited to the specific designs shown which are merely illustrative. Various and numerous other arrangements may be devised by one skilled in the art without departing from the spirit and scope of this invention. For example, pretension rivets, adjustable clips, preload self locking nut and bolt systems, and a rod with a plurality of apertures for receiving cotter pins to secure the upper hook to the lower hook could replace the hex bolts and threaded apertures as the means for securing the upper hook to the lower hook with the lamina therebetween. Therefore, the scope of the invention is defined in the following claims.

What is claimed is:

1. A lamina hook for attachment to a vertebra which includes a cranial side, a sacral side, a lamina and a spinous process with first and second lateral sides, the lamina hook comprising:

a single upper hook for attachment to the lamina under the spinous process on the cranial side of the vertebra, the upper hook having first and second upper arms extending from the upper hook for extending outwardly from the lamina;

a single lower hook for attachment to the lamina under the spinous process on the sacral side of the vertebra, the lower hook having a first lower arm extending outwardly from the lower hook for extending from the lamina on the first lateral side of the spinous process and a second lower arm extending outwardly from the lower hook for extending from the lamina on the second lateral side of the spinous process; and first and second means for attaching the upper hook to the lower hook, the first attaching means extending between the first arms of the upper and lower hooks on the first lateral side of the spinous process and the second attaching means extending between the second arms of the upper and lower hooks on the second lateral side of the spinous process.

2. A lamina hook as recited in claim 1 further comprising means for attaching a spine rod.

3. A lamina hook as recited in claim 2 wherein the spine rod attaching means comprises a clamp for attaching the spine rod.

4. A lamina hook as recited in claim 3 wherein the clamp is attached to at least one of the first and second arms of the lower hook.

5. A lamina hook as recited in claim 1 wherein the upper hook defines a triangle with an open center, the three sides of the triangle defined by the first and second arms and a third arm extending between the first and second arms.

6. A lamina hook as recited in claim 1 wherein each arm of the upper hook and the lower hook defines an aperture and the first and second means for attaching the upper hook to the lower hook comprises a pair of bolts extending through the apertures of the first and second arms of the upper and lower hooks.

7. A lamina hook as recited in claim 6 wherein the means for attaching the upper hook to the lower hook further comprises C-spacers that fit over a shaft over each of the bolts between the upper and lower hooks.

8. A lamina hook as recited in claim 6 wherein the means for attaching the upper hook to the lower hook further comprises a pair of lock washers to prevent rotation of the bolts.

9. A lamina hook for attachment to a vertebra which includes a cranial side, a sacral side, a lamina and a spinous process with first and second lateral sides, the lamina hook comprising:

a single upper hook capable of being attached to the lamina under the spinous process on the cranial side of the vertebra, the upper hook having first and second upper arms extending from the upper hook for extending outwardly from the lamina, each upper arm defining an aperture;

a single lower hook capable of being attached to the lamina under the spinous process on the sacral side of the vertebra, the lower hook having first and second lower arms extending from the lamina for extending outwardly from the lamina on either side of the spinous process, each lower arm defining an aperture; and a pair of shafts extending through the apertures of the arms of the upper and lower hooks on the lateral sides of the spinous process for attaching the upper hook to the lower hook.

10. A lamina hook as recited in claim 9 wherein the upper hook defines a triangle with an open center, the three sides of the triangle defined by the two upper arms and a third arm extending between the two upper arms.

11. A lamina hook as recited in claim 9 wherein the pair of shafts comprises a pair of bolts through the apertures of the lower hook and the upper hook, the bolts for being placed on either side of the spinous process.

12. A lamina hook as recited in claim 11 further comprising a pair of C-spacers that fit around the shafts between the upper and lower hooks for abutting against the upper and lower hooks.

13. A lamina hook as recited in claim 11 further comprising a pair of lock washers to prevent rotation of the bolts.

14. A lamina hook as recited in claim 9 further comprising means for attaching a spine rod.

15. A lamina hook as recited in claim 14 wherein the spine rod attaching means comprises a clamp.

16. A lamina hook as recited in claim 15 wherein the clamp is attached to at least one lower arm of the lower hook.

17. A lamina hook for attachment to a vertebra which includes a cranial side, a sacral side, a lamina and a spinous process with first and second lateral sides, the lamina hook comprising:

an upper hook for attachment to the lamina under the spinous process on the cranial side of the vertebra, the upper hook having first and second upper arms extending from the upper hook, outwardly from the lamina;

a lower hook for attachment to the lamina under the spinous process on the sacral side of the vertebra, the lower hook having first and second lower arms extending from the lower hook outwardly from the lamina; and first and second means for attaching the upper hook to the lower hook, the first attaching means extending between the first arm of the upper hook and the first arm of the lower hook on the first lateral side of the spinous process and the second attaching means extending between the second arm of the upper hook and the second arm of the lower hook on the second lateral side of the spinous process.

18. A lamina hook as recited in claim 17 further comprising means for attaching a spine rod.

19. A lamina hook as recited in claim 18 wherein the spine rod attaching means comprises a clamp.

20. A lamina hook as recited in claim 19 wherein the clamp is attached to at least one of the arms of the upper and lower hook.

21. A lamina hook as recited in claim 17 further comprising a pair of clamps for attaching a pair of spine rods.

22. A lamina hook as recited in claim 21 wherein each clamp is attached to an arm of the upper hook.

23. A lamina hook as recited in claim 21 wherein each clamp is attached to an arm of the lower hook.

24. A lamina hook as recited in claim 17 wherein each arm of the upper hook and the lower hook defines an aperture and the first and second means for attaching the upper hook to the lower hook comprises a pair of bolts extending through the apertures of the first and second arms of the upper and lower hooks.

25. A lamina hook as recited in claim 24 further comprising a first clamp on the first arm of the upper hook for attaching a first spine rod and a second clamp on the second arm of the upper hook for attaching a second spine rod.

26. A lamina hook as recited in claim 24 further comprising a first clamp on the first arm of the lower hook for attaching a first spine rod and a second clamp on the second arm of the lower hook for attaching a second spine rod.

27. A lamina hook for attachment to a vertebra which includes a cranial side, a sacral side, a lamina and a spinous process with first and second lateral sides, the lamina hook comprising:

an upper hook capable of being attached to the lamina under the spinous process on the cranial side of the vertebra, the upper hook having first and second upper arms extending from the upper hook for extending outwardly from the lamina, each upper arm including an aperture;

a lower hook capable of being attached to the lamina under the spinous process on the sacral side of the vertebra, the lower hook having first and second lower arms extending from the lamina for extending outwardly from the lamina, each lower arm including an aperture;

a first shaft for extending through the apertures of the first arms of the upper and lower hooks on the first lateral side of the spinous process for attaching the upper hook to the lower hook; and a second shaft for extending through the apertures of the second arms of the upper and lower hooks on the second lateral side of the spinous process for attaching the upper hook to the lower hook.

28. A lamina hook as recited in claim 27 wherein the first and second shafts comprise a pair of bolts.

29. A lamina hook as recited in claim 27 further comprising means for attaching a spine rod.

30. A lamina hook as recited in claim 29 wherein the spine rod attaching means comprises a clamp.

31. A lamina hook as recited in claim 30 wherein the clamp is attached to at least one arm of the upper and lower hooks.

32. A lamina hook as recited in claim 31 wherein the clamp comprises a saddle clamp.

33. A lamina hook as recited in claim 27 further comprising a pair of clamps for attaching a pair of spine rods.

34. A lamina hook as recited in claim 33 wherein each clamp is attached to an arm of the upper hook.

35. A lamina hook as recited in claim 33 wherein each clamp is attached to an arm of the lower hook.

36. A lamina hook as recited in claim 33 wherein the clamps comprise saddle clamps.

* * * * *